United States Patent
Seki et al.

(10) Patent No.: US 8,374,672 B2
(45) Date of Patent: Feb. 12, 2013

(54) BIOMAGNETIC FIELD MEASUREMENT APPARATUS CAPABLE OF EXACT POSITIONING

(75) Inventors: Yusuke Seki, Musashino (JP); Akihiko Kandori, Tokyo (JP); Mitsuru Oonuma, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1014 days.

(21) Appl. No.: 11/905,706

(22) Filed: Oct. 3, 2007

(65) Prior Publication Data

US 2008/0086049 A1 Apr. 10, 2008

(30) Foreign Application Priority Data

Oct. 6, 2006 (JP) ................................. 2006-274602

(51) Int. Cl.
*A61B 5/05* (2006.01)
(52) U.S. Cl. ...................................... 600/409; 324/300
(58) Field of Classification Search .......... 600/409–411, 600/415; 324/300, 301, 244, 248, 260, 261
See application file for complete search history.

(56) References Cited

U.S. PATENT DOCUMENTS

| | | | |
|---|---|---|---|
| 5,666,052 A * | 9/1997 | Sata .............................. | 324/248 |
| 8,010,178 B2 * | 8/2011 | Seki et al. ..................... | 600/409 |
| 2002/0115571 A1 * | 8/2002 | Yokosawa et al. ............ | 505/162 |

FOREIGN PATENT DOCUMENTS

| | | |
|---|---|---|
| JP | 05-212008 | 2/1992 |
| JP | 06-197879 | 12/1992 |
| JP | 06-197880 | 12/1992 |
| JP | 07-265276 | 3/1994 |
| JP | 09-327444 | 6/1996 |
| JP | 2000-139864 | 3/1999 |

OTHER PUBLICATIONS

S. J. Williamson et al., "Biomagnetism", Journal of Magnetism and Magnetic Materials, vol. 22 (1981), pp. 129-201.
Hidehiro Hosaka et al., "Part IV Visual Determination of Generators of the Magnetocardiogram", J. Electrocardiology, vol. 9. No. 4 (1976), pp. 426-432.

* cited by examiner

*Primary Examiner* — Parikha Mehta
(74) *Attorney, Agent, or Firm* — Stites & Harbison, PLLC; Juan Carlson A. Marquez, Esq; Stephen J. Weyer, Esq.

(57) ABSTRACT

There is provided a biomagnetic field measurement apparatus capable of carrying out exact positioning work and highly sensitive signal detection. To bring a sensor surface close to a body surface while the sensor surface and the body surface are kept parallel, a cryostat is constructed so as to be capable of oscillating and expanding and contracting. A gantry is formed by three supports. A first support is a portal support that supports the whole of the gantry. A second support is supported on the first support, and is rotatable with a first direction being the axis. A third support is supported on the second support, and is movable in the axial direction of the cryostat as viewed from the second support. The cryostat is supported on the third support, and moves integrally with the third support.

15 Claims, 23 Drawing Sheets

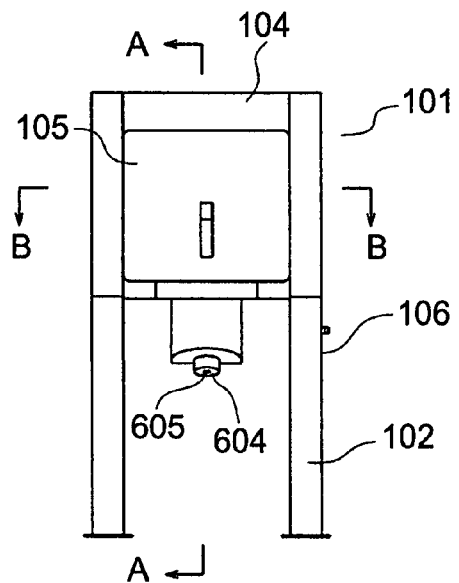
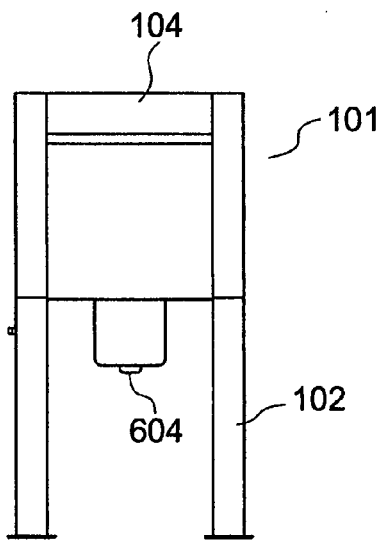
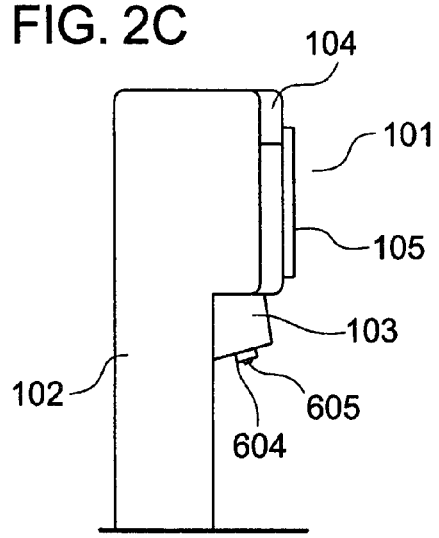
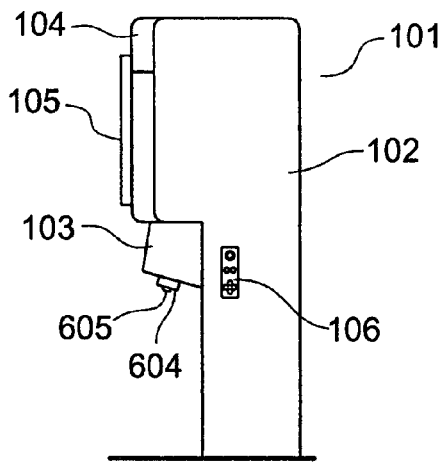
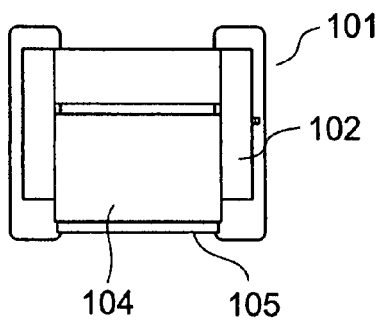
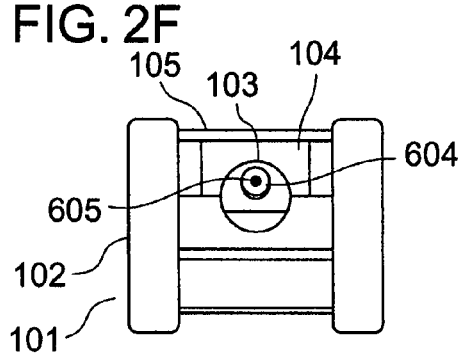

FIG. 21
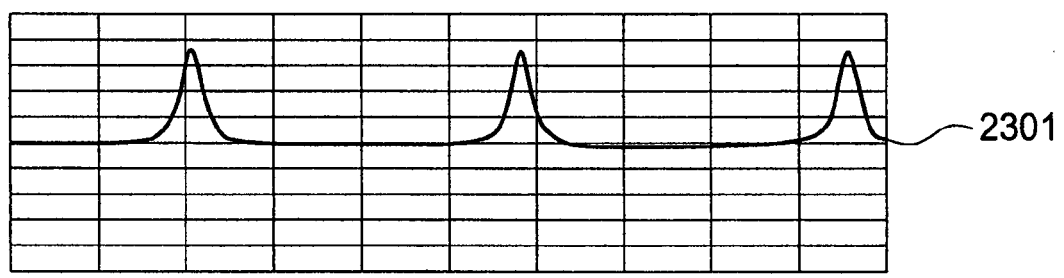
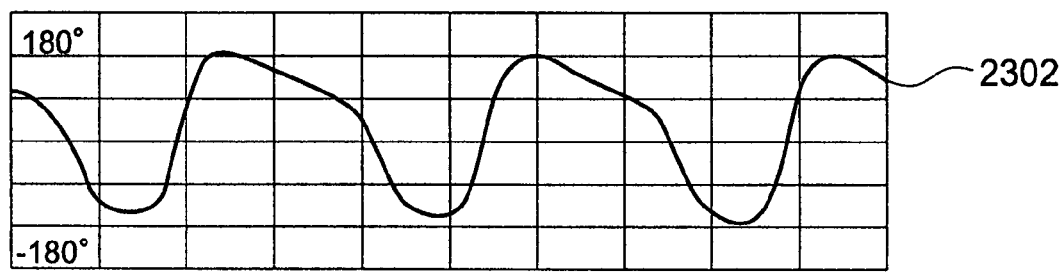
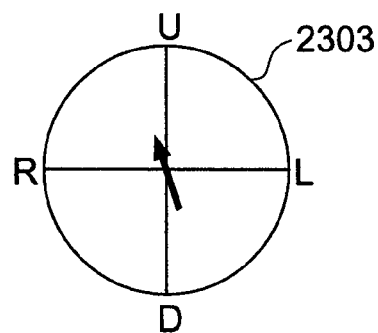

BIOMAGNETIC FIELD MEASUREMENT APPARATUS CAPABLE OF EXACT POSITIONING

INCORPORATION BY REFERENCE

The present application claims priority from Japanese application JP2006-274602 filed on Oct. 6, 2006, the content of which is hereby incorporated by reference into this application.

BACKGROUND OF THE INVENTION

1. Field of the Invention

The present invention relates to a biomagnetic field measurement apparatus for detecting a magnetic field generating mainly from the heart of an unborn child.

2. Description of the Related Art

For a magnetocardiograph that measures a magnetic field generating from the heart (heart magnetic field), it is necessary to bring a sensor close to the measurement portion of an examinee (the chest if the examinee is a grown-up person, the lower abdomen of mother's body if it is an unborn child). In the related art, the measurement position of sensor has been adjusted by vertically moving a cylindrical cryostat that holds the sensor or a bed on which the examinee lies. A problem with this method is that the signal intensity decreases because the sensor surface parallel with the horizontal plane is not necessarily parallel with the body surface. Especially when the heart magnetic field of unborn child is detected, it is necessary to bring the sensor surface close to the lower abdomen of mother's body, so that exact positioning is difficult to do.

To solve this problem, for example, in Patent Documents 1 to 6, ingenuity has been exercised in facilitating the positioning work by means of a mechanism for tilting the cryostat or a mechanism for moving the cryostat up and down that is added to a gantry.

Conventionally, a biomagnetic field measurement apparatus used for heart magnetic field measurement and brain magnetic field measurement has employed a method in which magnetic signals of a living body, which is a subject, are detected by a detector coil consisting of superconductive wiring and are transmitted to a superconducting quantum interference device (hereinafter abbreviated as SQUID). The detector coil plays a role in removing noise caused by the environmental magnetic field and thereby enhancing the signal-to-noise ratio (S/N ratio). The biomagnetism measurement and the detector coil have been explained in detail in Non-Patent Document 1.

[Patent Document 1] JP-A-7-265276
[Patent Document 2] JP-A-2000-139864
[Patent Document 3] JP-A-5-212008
[Patent Document 4] JP-A-6-197879
[Patent Document 5] JP-A-6-197880
[Patent Document 6] JP-A-9-327444
[Non-Patent Document 1] S. J. Williamson and L. Kaufman, Journal of Magnetism and Magnetic Materials, 22 (1981), 129-201

In the related art, the measurement position of sensor has been adjusted by vertically moving the cryostat that holds the sensor or the bed on which the examinee lies. This method has a problem in that the signal intensity decreases because the sensor surface is not necessarily parallel with the body surface. Also, even if the mechanism for tilting the cryostat or the mechanism for moving the cryostat up and down is added to the gantry, the cryostat must be moved up and down while being tilted. In this case, there arises a problem in that when the heart magnetic field of unborn child is measured, a sense of oppression is given to the examinee and the positioning work is difficult to do.

Also, as shown in Non-Patent Document 1 (FIG. 5), the conventional differential magnetism detector coil has been configured merely so that a magnetic field differentiated in certain one direction is detected. This method has a problem in that the environmental magnetic field is not reduced sufficiently in the case where the environmental magnetic field is strong, for example, in a magnetism shieldless environment. In order to reduce the environmental magnetic field, a method can be used in which the order of differential magnetism detector coil is increased. However, this method has a problem in that although the environmental magnetic field is reduced, the magnetic signals to be detected are also decreased.

SUMMARY OF THE INVENTION

The present invention has been made to solve the above problems, and accordingly an object thereof is to provide a biomagnetic field measurement apparatus capable of carrying out exact positioning work and highly sensitive signal detection. Specifically, an object of the present invention is to provide a biomagnetic field measurement apparatus capable of detecting living body magnetic signals of unborn child safely with high sensitivity by bringing a sensor surface close to the abdominal wall of mother's body safely and exactly.

In the biomagnetic field measurement apparatus according to the present invention, to bring the sensor surface close to a body surface while the sensor surface and the body surface are kept in parallel, a cryostat is constructed so as to be capable of oscillating and expanding and contracting. A gantry is formed by three supports. A first support is a portal support that supports the whole of the gantry. A second support is supported on the first support, and is rotatable with a first direction being the axis. A third support is supported on the second support, and is movable in the axial direction of the cryostat. The cryostat is supported on the third support, and moves integrally with the third support.

The gantry for holding the cryostat is of a portal type to restrain the vibrations of the cryostat.

The support part of gantry has a notch part so that an examiner can exactly check the positional relationship between the sensor surface and an examinee visually.

The tip end part of the cryostat has a surface tilting to the examinee side, and a sensor is provided on the tilting surface.

A cover on the front of the gantry is openable and closable by means of the hinge construction thereof to efficiently perform maintenance work such as supply of liquid helium, evacuation of cryostat, and exchange of sensor.

The surface of the cryostat is coated with a conductive coating material to shield electromagnetic waves.

The cryostat has a distance sensor for sensing a distance between the cryostat surface close to the detection surface of the magnetic sensor and the body surface of the examinee.

The cryostat has a pressure sensor for sensing a pressure applied to the cryostat surface, which is provided on the cryostat surface close to the detection surface of the magnetic sensor.

According to the present invention, by moving the position of the cryostat freely by oscillating motion and expanding and contracting motion, the sensor can be fixed at a position to be measured. As the result, the distance between the sensor and the signal source can be brought close to a minimum value, so that an effect can be achieved that the obtained signal intensity is higher than that of the conventional apparatus. Further, the measurement can be made both when the examinee adopts a sitting posture and when the examinee adopts a posture of lying on his/her back.

Other objects, features and advantages of the invention will become apparent from the following description of the embodiments of the invention taken in conjunction with the accompanying drawings.

BRIEF DESCRIPTION OF THE DRAWINGS

FIGS. 2A to 2F are six surface views of a magnetic field measurement apparatus in accordance with an embodiment of the present invention;

FIG. 21 is a graph showing the magnitude of an electric current vector obtained from the outputs of two sensors held in a cryostat (upper diagram), a graph showing the phase of the electric current vector obtained from the outputs of two sensors held in the cryostat (middle diagram), and a diagram showing the electric current vector obtained from the outputs of two sensors held in the cryostat (lower diagram);

DETAILED DESCRIPTION OF THE INVENTION

Figure 1:
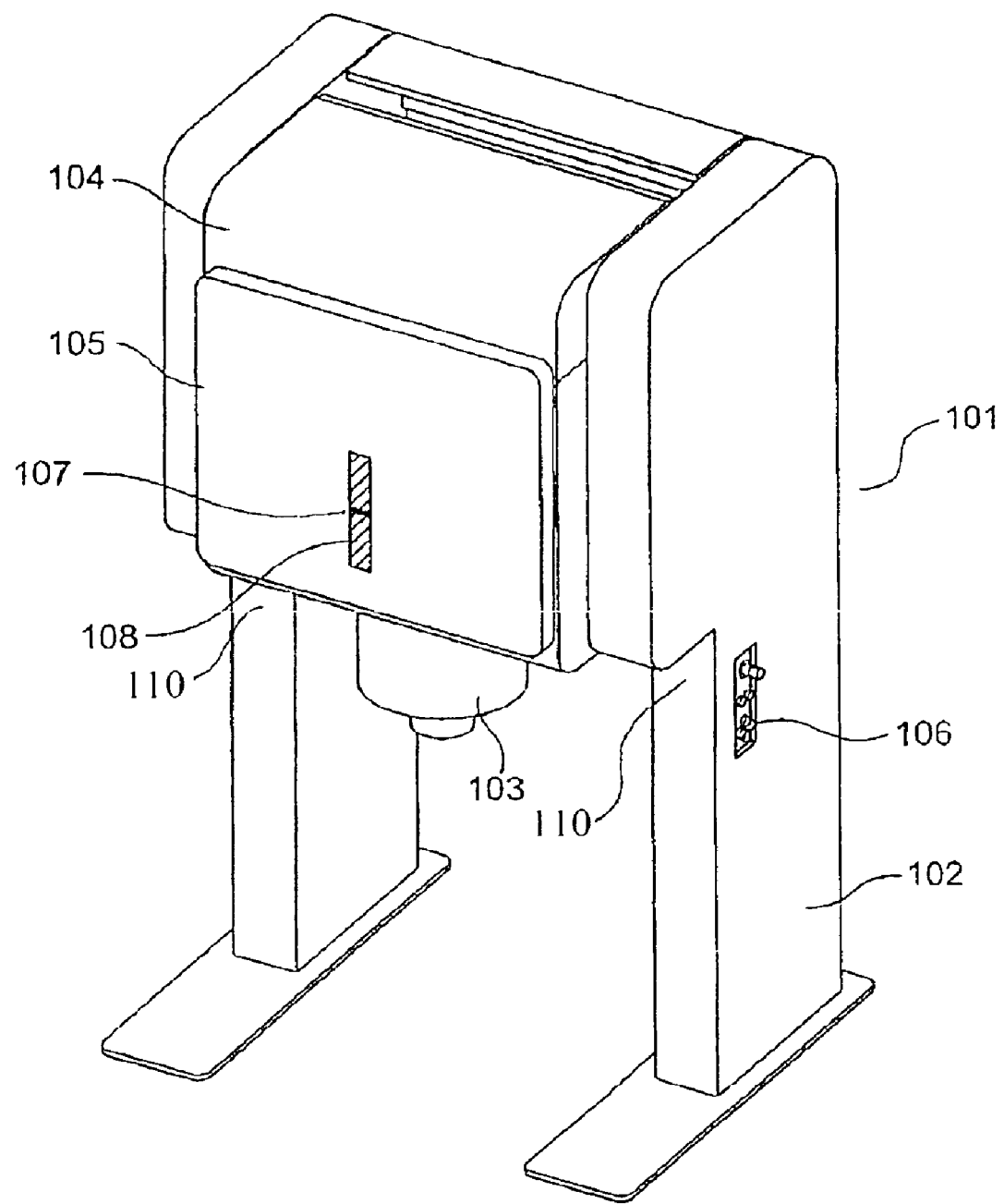
FIG. 1 is a perspective view of a magnetic field measurement apparatus in accordance with an embodiment of the present invention.

An embodiment of the present invention will now be described in detail with reference to the accompanying drawings. In the drawings, the same reference numerals are applied to elements having the same function.

As a superconductive material forming a detector coil used in an apparatus in the embodiment described below, a low-temperature superconductive material having a low superconductive transition temperature that acts as a superconductor at a low temperature (for example, the liquid helium temperature) or a high-temperature superconductive material having a high-temperature superconductive transition temperature that acts as a superconductor at a high temperature (for example, the liquid nitrogen temperature) can be used. A superconductive material having a superconductive transition temperature between the liquid helium temperature and the liquid nitrogen temperature or a superconductive material having a superconductive transition temperature higher than the liquid nitrogen temperature may be used. Also, a member forming the detector coil can use a metal having a high electrical conductivity, such as copper.

Figure 3A:
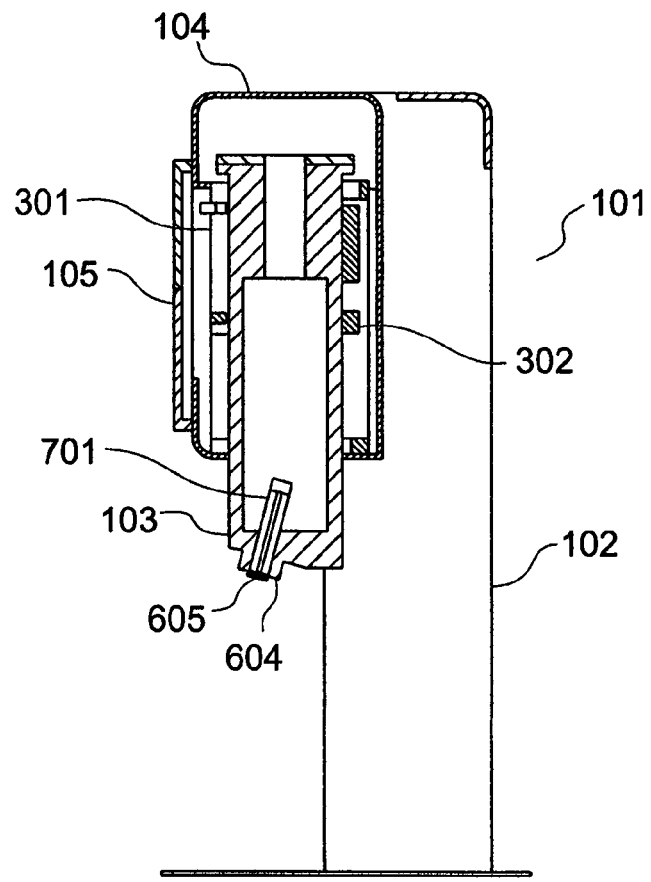
FIGS. 3A and 3B are sectional views of a magnetic field measurement apparatus in accordance with an embodiment of the present invention.
Figure 3B:
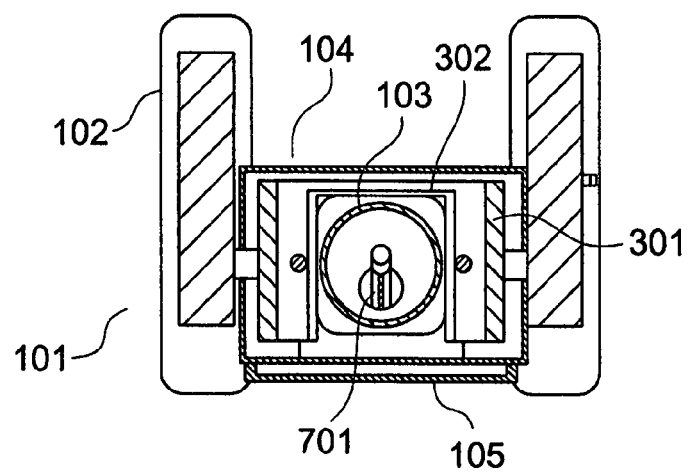

FIG. 1 is a perspective view of a magnetic field measurement apparatus in this embodiment. FIGS. 2A to 2F are six surface views of the magnetic field measurement apparatus in this embodiment, FIG. 2A being a front view, FIG. 2B being a back view, FIG. 2C being a left side view (showing the left-side surface viewed from the front), FIG. 2D being a right side view (showing the right-side surface viewed from the front), FIG. 2E being a top view, and FIG. 2F being a bottom view. FIGS. 3A and 3B are sectional views of the magnetic field measurement apparatus in this embodiment, FIG. 3A being a sectional view taken along the line A-A of FIG. 2A, and FIG. 3A being a sectional view taken along the line B-B of FIG. 2A. A cryostat 103 has a detection surface 604 tilting with respect to the horizontal plane, and holds a SQUID fluxmeter near the detection surface 604. In the conventional cryostat, the detection surface is often substantially parallel with the horizontal plane. This is because such a configuration is suitable for the measurement of the heart magnetic field of a grown-up person. On the other hand, in the state in which the mother's body lies on her back, the body surface of abdomen tilts with respect to the horizontal plane, so that it is difficult to bring the detection surface close to the measurement portion. Therefore, such a configuration is unsuitable for the measurement of the heart magnetic field of unborn child. Further, if the cryostat is tilted through an angle of about 30 degrees or larger, there arises a problem in that a refrigerant such as liquid helium filled therein evaporates rapidly. In the present invention, since the cryostat 103 is configured so that the detection surface 604 thereof tilts with respect to the horizontal plane, the positioning of the detection surface 604 with respect to the measurement portion of the abdomen of mother's body is made easy, and also the detection surface 604 can be adjusted so as to be in parallel with the body surface of abdomen of the mother's body without tiling the cryostat 103 greatly.

A magnetic field measurement apparatus 101 is made up of the cryostat 103 for keeping the SQUID fluxmeter at a low temperature and fixing it and a gantry for supporting and driving the cryostat 103. A first support 102 is a part of the structure of the gantry, and supports the whole of the gantry. The first support 102 can restrain the vibrations of the gantry by means of the portal construction. By restraining the vibrations of the gantry, the vibrations of the SQUID fluxmeter held in the cryostat 103 are restrained, so that an effect of reducing magnetic noise caused by vibrations can be achieved.

A gantry front cover 105 is a part of the structure of the gantry, and is openable and closable by means of the hinge construction thereof. Usually, the magnetic field measurement apparatus 101 is used in the state in which the gantry front cover 105 is closed. However, when the maintenance work for the cryostat 103 is performed, the gantry front cover 105 is opened. Since the hinge construction is used, an effect can be achieved that the maintenance work can be performed efficiently without the need for removing the whole of the gantry front cover 105. Also, a controller 106 is used to drivingly operate the gantry. Also, a cryostat position indicator 107 is provided at the central position of the gantry front cover 105 so that the position of the cryostat 103 can be checked by using the cryostat position indicator 107 through a transparent member 108.

It is desirable that all of the gantry and the cryostat forming the magnetic field measurement apparatus 101 be formed of a nonmagnetic material. In this embodiment, the gantry is formed of aluminum or brass, and the cryostat is formed of FRP (fiber reinforced plastics). In the perspective view of FIG. 1, the slanted parallel lines of the transparent member 108 are not lines appearing in appearance, and, for convenience, indicate that the portion is transparent.

Figure 4:
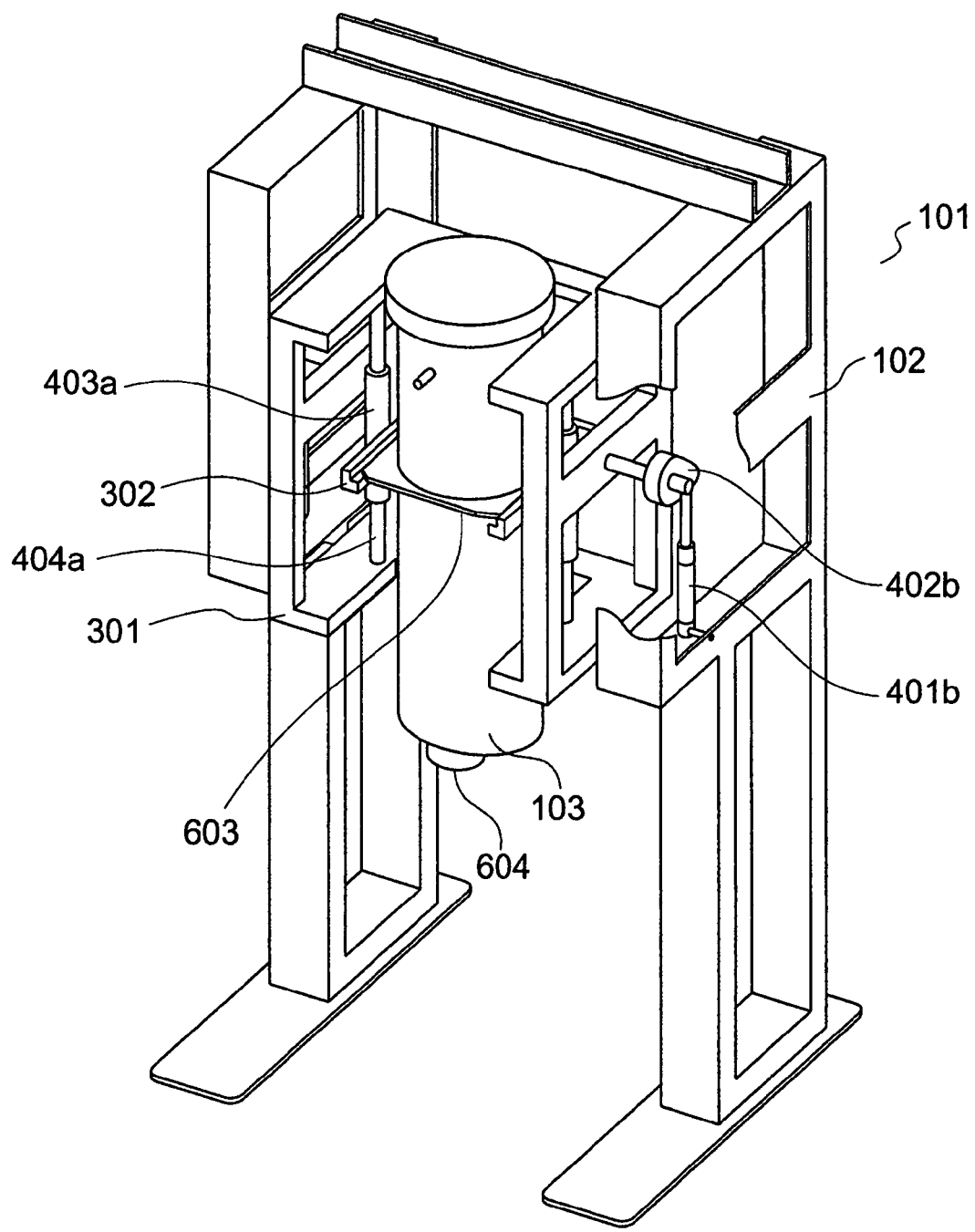
FIG. 4 is a perspective view showing a detailed construction of a gantry in accordance with an embodiment of the present invention.
Figure 5:
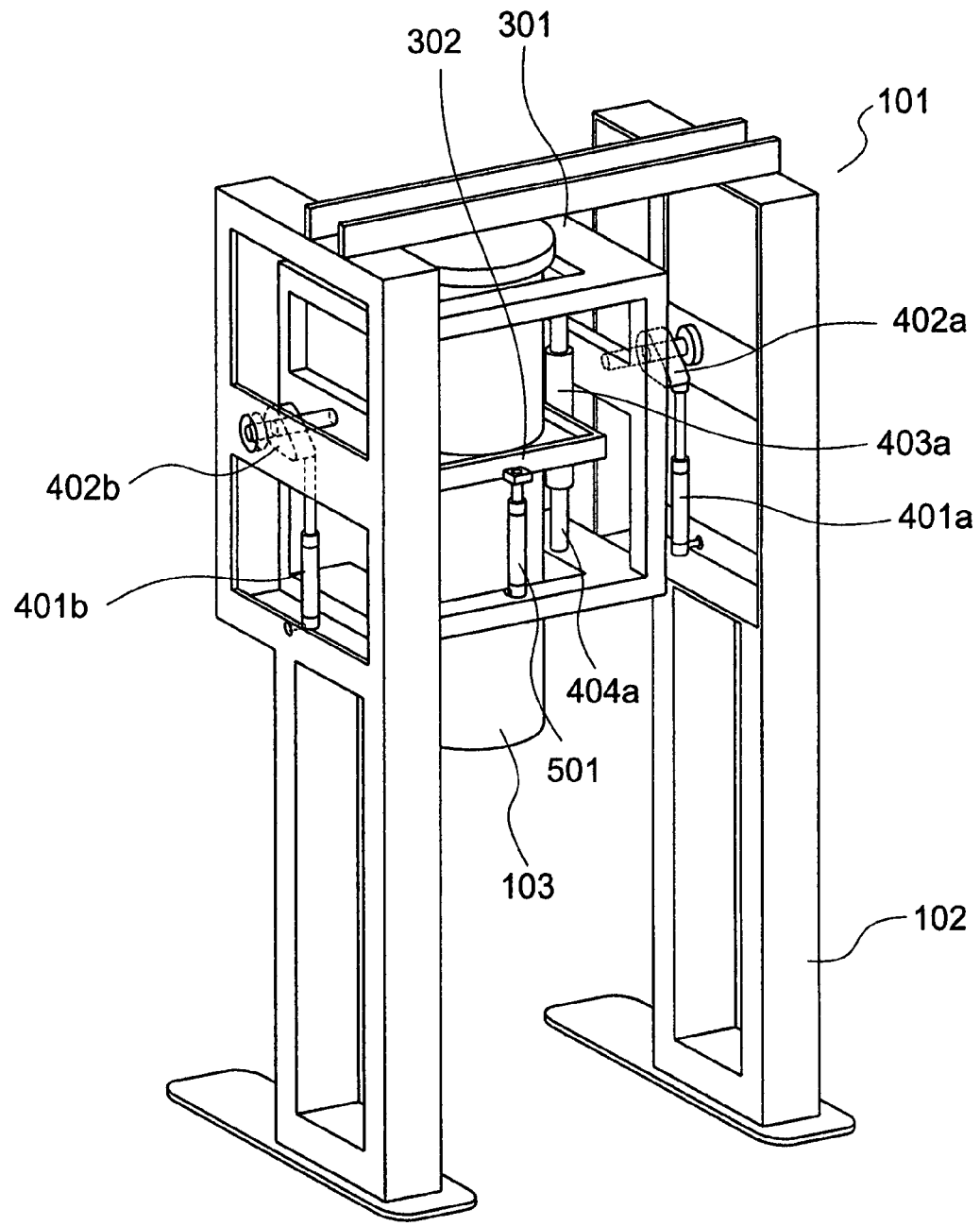
FIG. 5 is a perspective view showing a detailed construction of a gantry in accordance with an embodiment of the present invention.

FIGS. 4 and 5 are perspective views showing a detailed construction of the gantry in this embodiment. The first support 102 is fixed to the floor surface to support the whole of the gantry. The first support 102 supports a second support 301, and rotationally drives the second support 301 with a first direction being the axis of rotation by means of driving means 401a and 401b and cranks 402a and 402b. The driving means 401a and 401b each is formed by a hydraulic cylinder. By expanding and contracting the hydraulic cylinders, the cranks 402a and 402b fixed to the second support is turned, and resultantly the second support is also turned with the first direction being the axis of rotation. The first direction (direction of rotation axis) is substantially perpendicular to a second direction (lengthwise direction) parallel with the axis of the cylindrical cryostat 103, and is a direction such that both leg parts of the first support 102 are connected to each other. The detection surface 604 at the tip end of the cryostat 103 oscillates with the first direction being the axis of rotation. The oscillation angle of the axis of the cryostat 103 with respect to the vertical direction is preferably in the range of +30 degrees to −30 degrees from the viewpoint of measurement.

The second support 301 supports a third support 302, and drives the third support 302 in the second direction by means of a driving means 501. Specifically, the driving means 501 is formed by a hydraulic cylinder, and is fixed between the second support 301 and the third support 302. By expanding and contracting the hydraulic cylinder, the third support 302 moves in the second direction, which is the axial direction of the cryostat, as viewed from the second support 301. At both ends of the third support 302, guide mechanisms 403a and 403b are fixed. The guide mechanisms 403a and 403b move in the second direction along rails 404a and 404b fixed to the second support 301. As the result, the third support 302 can move in the second direction smoothly. Further, the cryostat 103 is fixed to the third support 302 via an intermediate flange 603. The cryostat 103 is rotationally driven (oscillated) with the first direction being the axis of rotation, and is further driven in the second direction (expanded and contracted).

Figure 6:
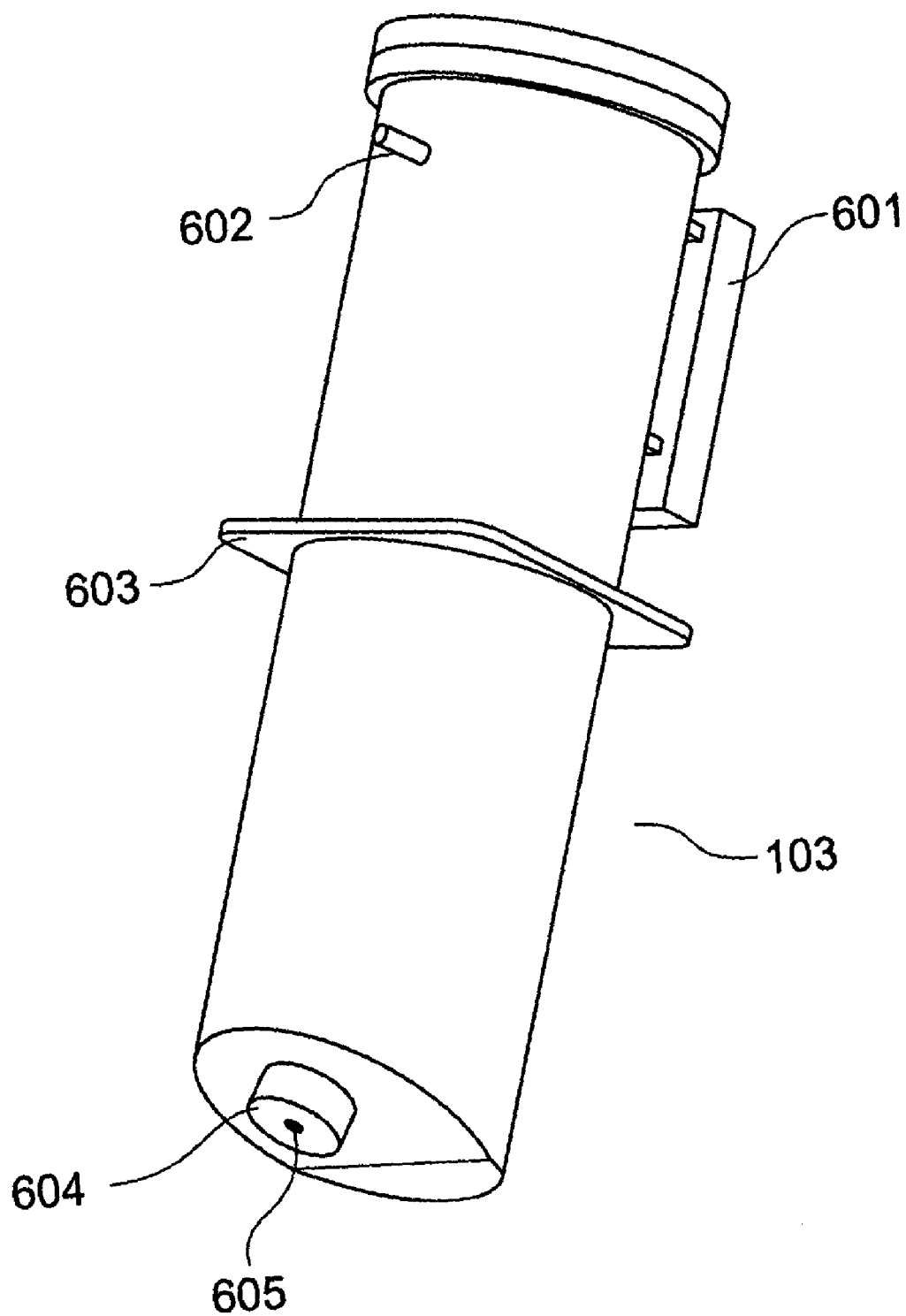
FIG. 6 is a perspective view of a cryostat in accordance with an embodiment of the present invention.

FIG. 6 is a perspective view of the cryostat in this embodiment. FIGS. 7A to 7F are six surface views of the cryostat 103 in this embodiment, FIG. 7A being a front view, FIG. 7B being a back view, FIG. 7C being a left side view (showing the left-side surface viewed from the front), FIG. 7D being a right side view (showing the right-side surface viewed from the front), FIG. 7E being a top view, and FIG. 7F being a bottom view.

The cryostat 103 is a vacuum insulated vessel, and is used to keep the SQUID fluxmeter at a low temperature by being filled with liquid helium. An FLL circuit 601 for driving the SQUID fluxmeter is fixed to the side surface of the cryostat 103. If the cable connecting the SQUID fluxmeter to the FLL circuit is long, the signal diminishes, and also noise is easily introduced. Therefore, the cable is preferably as short as possible. In this embodiment, by fixing the FLL circuit 601 to the side surface of the cryostat 103, the cable connecting the SQUID fluxmeter to the FLL circuit can be made short. An evacuation port 602 is arranged so as to be present at the front position in the state in which the cryostat 103 is fixed to the gantry. As the result, evacuation work can be performed in the state in which the cryostat 103 is fixed to the gantry. The cryostat 103 is fixed to the gantry by fixing the intermediate flange 603 to the third support 302 (refer to FIG. 4) and is driven.

Also, the detector coil of the SQUID fluxmeter is fixed to the vicinity of the detection surface 604 in the cryostat 103. As shown in FIG. 6, the detection surface 604 has a shape projecting from the side surface of the cryostat 103, by which the detection surface 604 can easily be aligned with the measurement position of abdomen of a pregnant woman, and also an effect of alleviating a sense of oppression given to the examinee can be achieved. Further, the detection surface 604 is allowed to have a tilt from a plane perpendicular to the axial direction of the cryostat 103 (the second direction), by which the detection surface 604 can be tilted greatly with respect to the horizontal plane. In this embodiment, the detection surface 604 has a tilt of 15 degrees from the plane perpendicular to the axial direction of the cryostat 103 (the second direction). In the state in which the mother's body lies on her back, the tilt angle of the abdomen surface with respect to the horizontal plane is substantially smaller than 45 degrees. Therefore, as described later, in the case where the cryostat is configured so as to be capable of being tilted to 30 degrees, if the tilt of the detection surface is from 15 degrees to about 30 degrees, the detection surface can be brought to a position substantially parallel with the body surface in the measurement portion even when the abdomen surface of mother's body is substantially horizontal with respect to the horizontal plane or even when the abdomen surface tilts through 45 degrees. As the result, the positioning work can be performed with high accuracy.

Usually, the cryostat 103 cannot be tilted excessively because it is filled with liquid helium. In this embodiment, the oscillation angle of the cryostat 103 is variable in the range of +30 degrees to −30 degrees from the state in which the second direction is the vertical direction. Paying attention to the absolute value of the angle that the detection surface makes with the horizontal plane, in the case where the detection surface is the surface perpendicular to the second direction, the angle changes in the range of 0 degree to 30 degrees, whereas in this embodiment, the angle changes in the range of 0 degree to 45 degrees. That is to say, according to this embodiment, the angle of the detection surface 604 can be changed by the same oscillation angle. By increasing the angle range of the detection surface 604, the positioning of the detection surface 604 with respect to the body surface of the examinee can be performed more exactly. Further, the measurement can be made even in the state in which the examinee sits.

Figure 12:
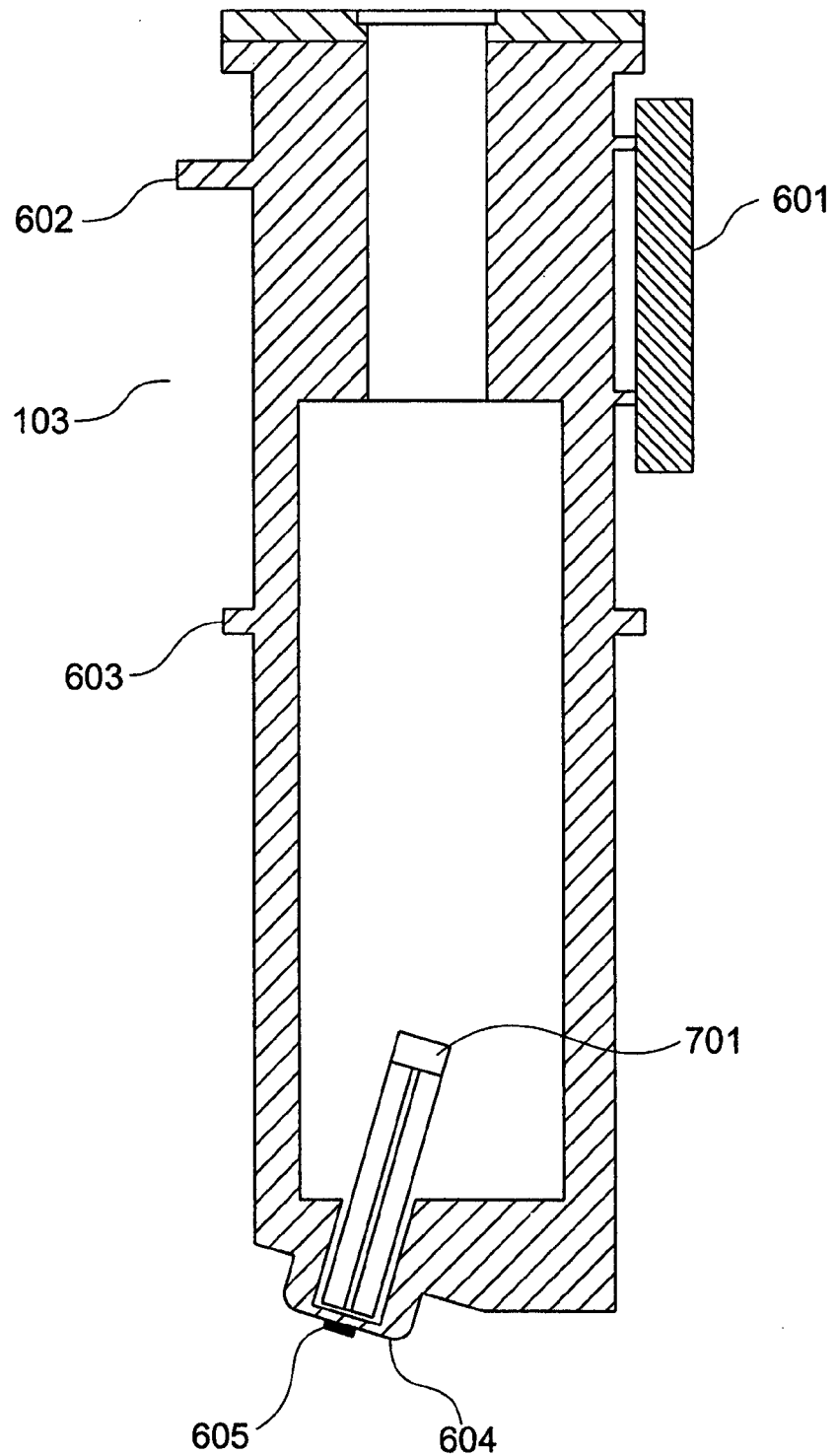
FIG. 12 is a sectional view of a cryostat in accordance with an embodiment of the present invention.

Also, by decreasing the area of the detection surface 604, the thicknesses of a vacuum layer, a dua outer layer, and a dua inner layer between the detector coil and the detection surface 604 can be decreased (FIG. 12). As the result, the distance between the signal source and the detector coil decreases, so that an effect of increased signal intensity can be achieved.

Also, the surface of the cryostat 103 is coated with a conductive coating material containing a metal having high electrical conductivity, such as sliver. This conductive coating material has an effect of shielding electromagnetic waves. The electromagnetic waves exert an adverse influence such that not only ambient noise is produced but also the detection sensitivity of SQUID is reduced. Conventionally, the electromagnetic waves have been shielded by placing the cryostat in a magnetic shield room formed of Permalloy or aluminum. On the other hand, in this embodiment, the cryostat 103 itself is allowed to have a function of shielding electromagnetic waves, by which the electromagnetic waves can be shielded without the use of the magnetic shield room. Also, by fixing the FLL circuit 601 to the cryostat 103 using screws of non-magnetic metal such as brass or stainless steel (SUS), the conductive coating material applied to the cryostat 103 can be grounded to the ground of the FLL circuit 601. As the result, the conductive coating material can function stably as an electromagnetic wave shield.

Also, the cryostat 103 may be provided with a pressure sensor for sensing a pressure applied to the surface of the detection surface 604. By this pressure sensor, an excessive pressure caused by the contact of the detection surface 604 of the cryostat 103 with the examinee can be measured to prevent such an excessive pressure. Similarly, a distance sensor may be provided on the cryostat 103 or the gantry to sense the distance between the detection surface 604 of the cryostat 103 and the body surface of the examinee. By this distance sensor, the distance between the detection surface 604 of the cryostat 103 and the examinee can be measured. Therefore, the contact of the detection surface 604 of the cryostat 103 with the examinee can be prevented, and also the positioning of the detection surface 604 can be controlled automatically.

Figure 8:
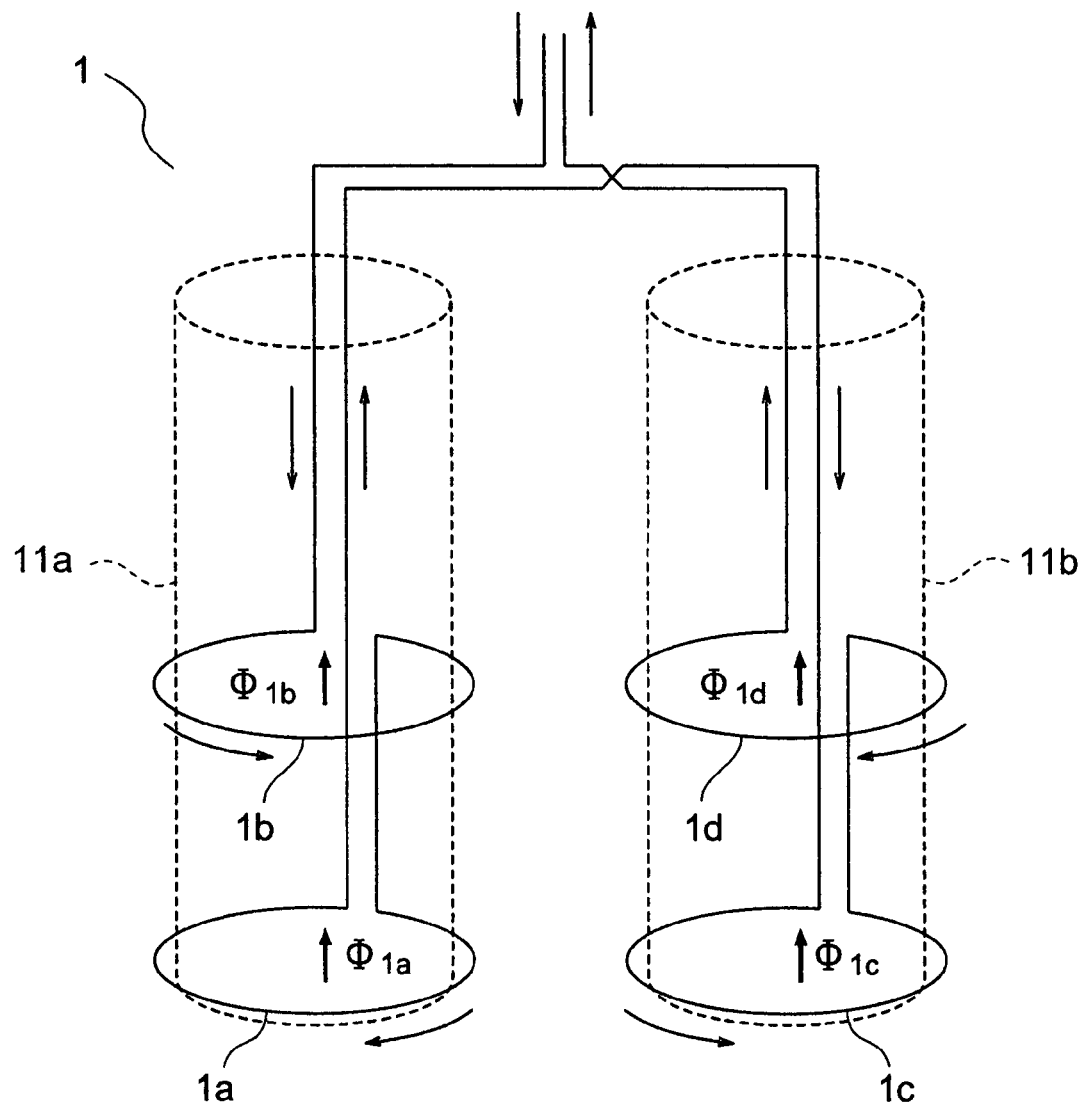
FIG. 8 is a first perspective view of a detector coil in accordance with an embodiment of the present invention.

FIG. 8 is a perspective view of the detector coil in this embodiment.

A detector coil 1 has a coil 1a formed by winding a superconductive wire one turn in a first direction around a bobbin 11a, a coil 1b formed by winding the superconductive wire one turn in a second direction opposite to the first direction at a place at a predetermined distance apart from the coil 1a vertically, a coil 1c formed by winding the superconductive wire one turn in the second direction around a bobbin 11b that is present at a place at a predetermined distance apart from the coil 1a horizontally, and a coil 1d formed by winding the superconductive wire one turn in the first direction at a place at a predetermined distance apart from the coil 1c vertically. That is to say, the detector coil 1 consists of one wire. In this configuration, the coil 1a and the coil 1c are present on the same plane, and the coil 1b and the coil 1d are present on the same plane. That is to say, a plurality of first-order differential coils are arranged in parallel at predetermined intervals. By this configuration, a magnetic flux $\Phi_{P1}$ described below (Expression 1) that is detected by the detector coil 1 can be expressed as follows by using a magnetic flux $\Phi_{1a}$ penetrating the coil 1a, a magnetic flux $\Phi_{1b}$ penetrating the coil 1b, a magnetic flux $\Phi_{1c}$ penetrating the coil 1c, and a magnetic flux $\Phi_{1d}$ penetrating the coil 1d.

$$\Phi_{P1}=(\Phi_{1a}-\Phi_{1b})-(\Phi_{1c}-\Phi_{1d}) \quad \text{(Expression 1)}$$

That is to say, the detector coil 1 in this embodiment is a detector coil subjected to first-order differentiation in the axial direction (vertical direction) of the bobbin 11a (first term) and the bobbin 11b (second term), and at the same time, subjected to first-order differentiation in the horizontal direction. Thus, the detector coil 1 detects magnetic signals that are subjected to first-order differentiation in the vertical direction and further subjected to first-order differentiation in the horizontal direction. Therefore, the environmental magnetic field can be reduced as compared with the case where a first-order differential detector coil is used.

Figure 9:
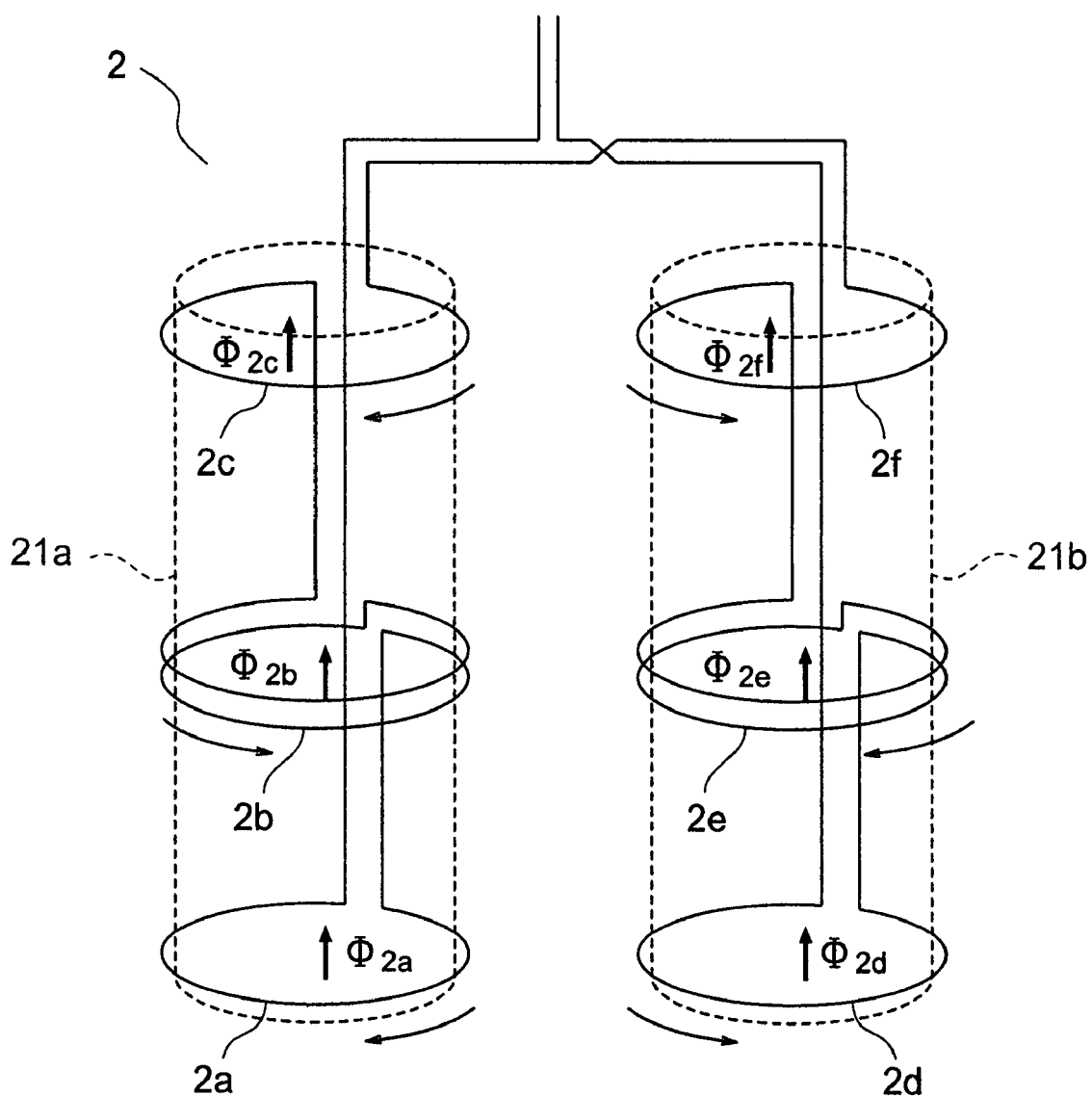
FIG. 9 is a second perspective view of a detector coil in accordance with an embodiment of the present invention.

FIG. 9 is a perspective view of a detector coil in this embodiment.

A detector coil 2 in this embodiment has a coil 2a formed by winding a superconductive wire one turn in a first direction around a bobbin 21a, a coil 2b formed by winding the superconductive wire two turns in a second direction opposite to the first direction at a place at a predetermined distance apart from the coil 2a vertically, a coil 2c formed by winding the superconductive wire one turn in the first direction at a place at a predetermined distance apart further from the coil 2b vertically, a coil 2d formed by winding the superconductive wire one turn in the second direction around a bobbin 21b that is present at a place at a predetermined distance apart from the coil 2a horizontally, a coil 2e formed by winding the superconductive wire two turns in the first direction at a place at a predetermined distance apart from the coil 2d vertically, and a coil 2f formed by winding the superconductive wire one turn in the second direction at a place at a predetermined distance apart further from the coil 2e vertically. That is to say, the detector coil 2 consists of one wire. In this configuration, the coil 2a and the coil 2d are present on the same plane, the coil 2b and the coil 2e are present on the same plane, and the coil 2c and the coil 2f are present on the same plane. That is to say, a plurality of second-order differential coils are arranged in parallel at predetermined intervals. By this configuration, a magnetic flux $\Phi_{P2}$ described below (Expression 2) that is detected by the detector coil 2 can be expressed as follows by using a magnetic flux $\Phi_{2a}$ penetrating the coil 2a, a magnetic flux $\Phi_{2b}$ penetrating the coil 2b, a magnetic flux $\Phi_{2c}$ penetrating the coil 2c, a magnetic flux $\Phi_{2d}$ penetrating the coil 2d, a magnetic flux $\Phi_{2e}$ penetrating the coil 2e, and a magnetic flux $\Phi_{2f}$ penetrating the coil 2f.

$$\Phi_{P2}=(\Phi_{2a}-2\Phi_{2b}+\Phi_{2c})-(\Phi_{2d}-2\Phi_{2e}+\Phi_{2f}) \quad \text{(Expression 2)}$$

That is to say, the detector coil 2 in this embodiment is a detector coil subjected to second-order differentiation in the axial direction (vertical direction) of the bobbin 21a (first term) and the bobbin 21b (second term), and at the same time, subjected to first-order differentiation in the horizontal direction. Thus, the detector coil 2 detects magnetic signals that are subjected to second-order differentiation in the vertical direction and further subjected to first-order differentiation in the horizontal direction. Therefore, the environmental magnetic field can be reduced as compared with the case where a second-order differential detector coil is used.

The detector coils shown in FIGS. 8 and 9 each have a circular coil shape. However, the coil shape is not limited to this shape, and, for example, a coil having a polygonal shape may be used.

Next, one example of a method for arranging detector coils in this embodiment is explained with reference to FIG. 10 and FIGS. 11A and 11B while referring to FIG. 9.

Figure 10:
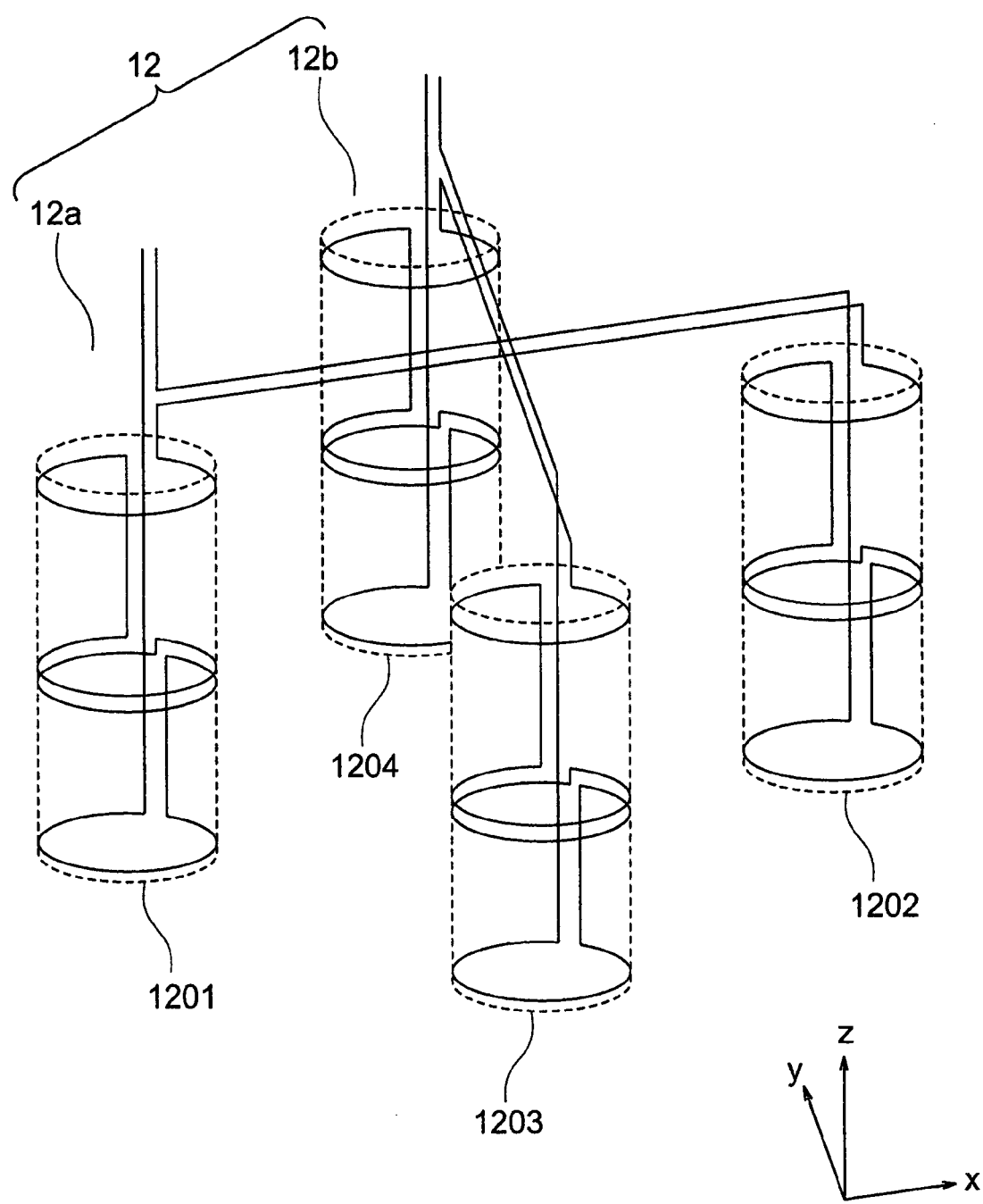
FIG. 10 is a perspective view showing arrangement of detector coils in accordance with an embodiment of the present invention.

FIG. 10 is a perspective view showing the arrangement of detector coils in this embodiment.

Detector coils 12a and 12b each have the same configuration as that of the detector coil 2 shown in FIG. 10. Each of both the detector coils 12a and 12b is configured so as to have a pair of differential coils. The detector coil 12a consists of a coil 1201 having a configuration of second-order differential detector coil and a coil 1202 having a winding direction opposite to that of the coil 1201. Similarly, the detector coil 12b consists of a coil 1203 having a configuration of second-order differential detector coil and a coil 1204 having a winding direction opposite to that of the coil 1201. Hereunder, the set of the detector coils 12a and 12b is described as a detector coil set 12. The detector coil set 12 is characterized in that the detector coils 12a and 12b are arranged so that the directions of first-order differentiation in the horizontal direction intersect with each other at right angles.

Figure 11A:
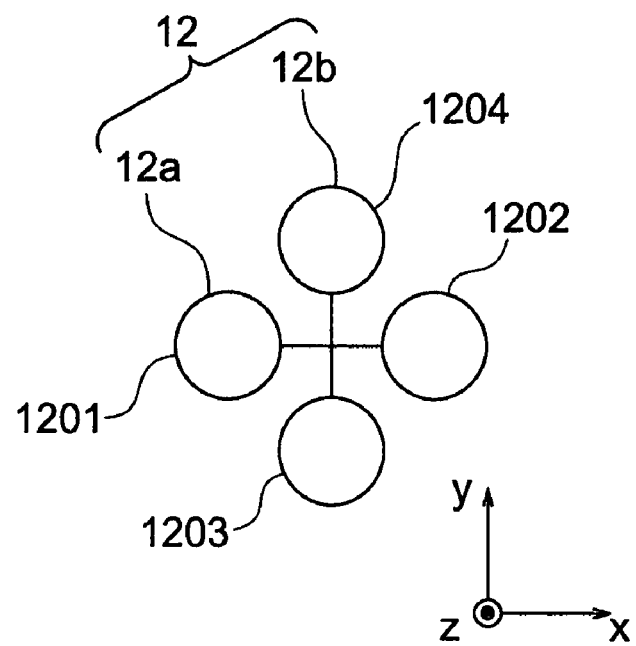
FIG. 11A is a top view schematically showing a set of detector coils shown in FIG. 10.
Figure 11B:
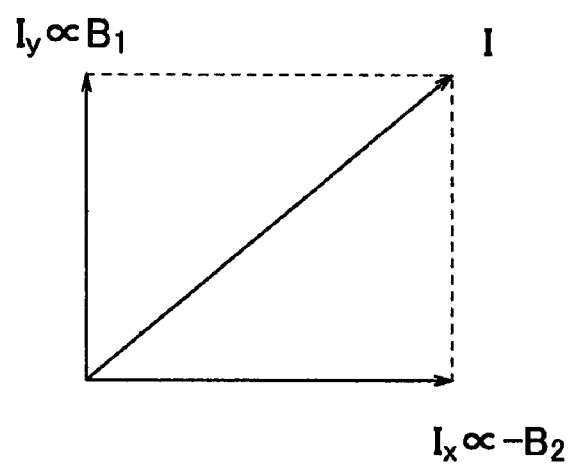
FIG. 11B is a diagram showing an electric current vector, which is a magnetic field source, and the relationship between a Z-direction magnetic field flux density subjected to first-order differentiation in the x-axis direction and a Z-direction magnetic flux density subjected to first-order differentiation in the y-axis direction, which are detected by detector coils.

FIG. 11A is a top view schematically showing the detector coil set shown in FIG. 10. FIG. 11B is a diagram showing the relationship between an electric current vector, which is a magnetic field source, and a Z-direction magnetic flux density $B_1$ subjected to first-order differentiation in the x-axis direction, which is detected by the detector coil 12a, and a Z-direction magnetic flux density $B_2$ subjected to first-order differentiation in the y-axis direction, which is detected by the detector coil 12b.

Generally, in the case where an electric current such as a myocardial electric current flows in the x-axis direction, in order to detect a magnetic field from which the electric current generates, magnetic signals can be detected by using a detector coil differentiated in the y-axis direction in FIG. 11A. On the other hand, in the case where a detector coil differentiated in the x-axis direction is used, signals are scarcely detected. Thus, in the case where a detector coil differentiated in the horizontal direction is used, it is desirable to use a detector coil differentiated in the direction intersecting at right angles with the direction of the electric current, which is a magnetic field source. However, in the case where the direction of electric current to be measured is unknown in advance as in the case of the myocardial electric current, it is desirable to arrange two detector coils of this embodiment in a form of intersecting with each other at right angles similarly to the detector coil set 12 as shown in FIG. 10.

Further, taking the magnetic flux density detected by the detector coil 12a as $B_1$ and the magnetic flux density detected by the detector coil 12b as $B_2$, the following expression, which is a vector sum of the magnetic flux densities, can be calculated.

$$B_0=\sqrt{(B_1^2+B_2^2)} \quad \text{(Expression 3)}$$

By calculating Expression 3, a magnetic field from which the electric current source generates can be detected surely regardless of the direction of electric current source to be measured.

Also, taking the electric current vector, which is a magnetic field source, as $I=(I_x, I_y)$, the x component $I_x$ of electric current and the y component $I_y$ of electric current each are approximately expressed by the following expression using a change in magnetic flux density in the z direction that is subjected to first-order differentiation in the x-axis direction $\Delta B_z/\Delta x$ and a change in magnetic flux density in the z direction that is subjected to first-order differentiation in the y-axis direction $\Delta B_z/\Delta y$, respectively (refer to H. Hosaka and D. Cohen, "Visual determination of generators of the magnetocardiogram", Journal of Electrocardiology (U.S.), 1976, Vol. 9, p 426-432).

$$(I_x, I_y) \propto (-\Delta B_z/\Delta y, \Delta B_z/\Delta x) \quad \text{(Expression 4)}$$

Therefore, the x component $I_x$ of electric current, which is a magnetic field source, and the y component $I_y$ of electric current each are approximately expressed by the following expression using the Z-direction magnetic flux density $B_1$ subjected to first-order differentiation in the x-axis direction, which is detected by the detector coil 12a, and the Z-direction magnetic flux density $B_2$ subjected to first-order differentiation in the y-axis direction, which is detected by the detector coil 12b.

$$(I_x, I_y) \propto (-B_2, B_1) \quad \text{(Expression 5)}$$

Therefore, the detector coil set 12 can detect the electric current, which is a magnetic field source, approximately as an electric current vector. That is, as shown in FIG. 11B, the electric current can be expressed as a vector by using the magnetic flux densities $B_1$ and $B_2$ detected by the detector coils 12a and 12b, respectively.

Thus, by arranging a plurality of detector coil sets 12, the magnetic field distribution can be detected. Further, by using Expression 5, the distribution of electric current vectors, which are magnetic field sources, (electric current vector field) can be detected. Thereby, regarding the brain magnetic field measurement, a portion where a nerve electric current flows can be estimated without caring about the direction in which the nerve electric current flows.

Figure 7A:
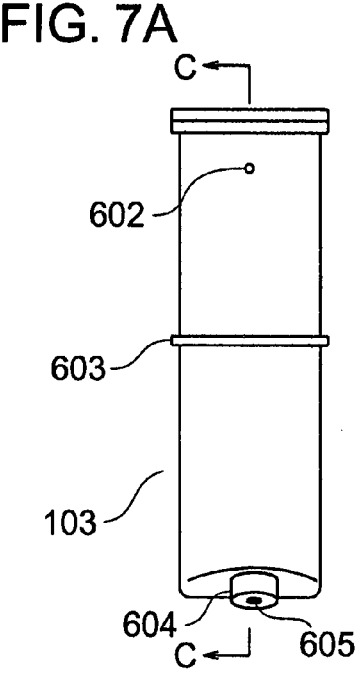
FIGS. 7A to 7F are six surface views of a cryostat in accordance with an embodiment of the present invention.
Figure 7B:
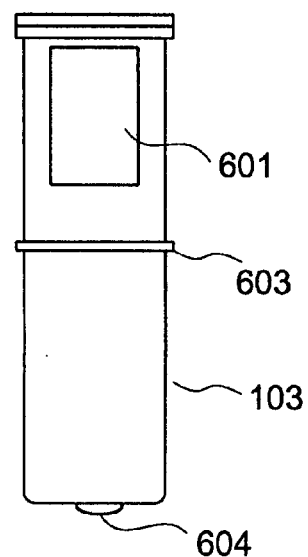
Figure 7C:
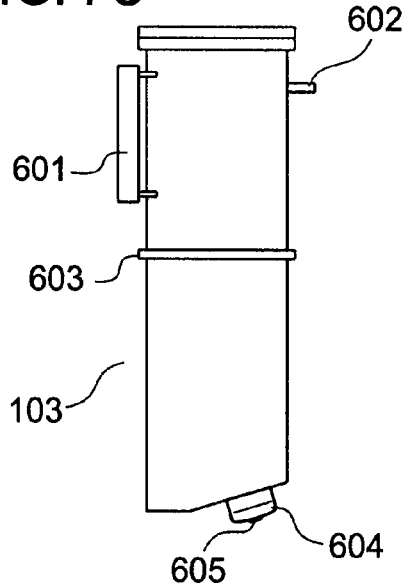
Figure 7D:
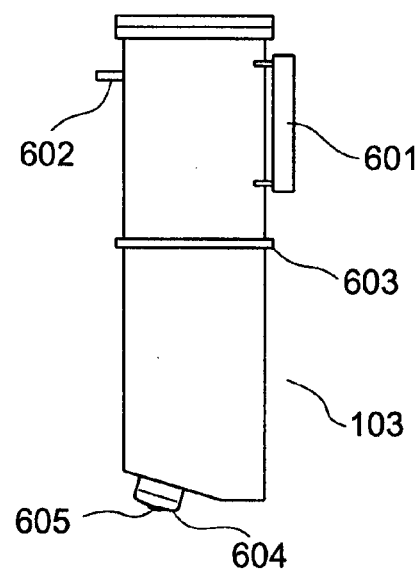
Figure 7E:
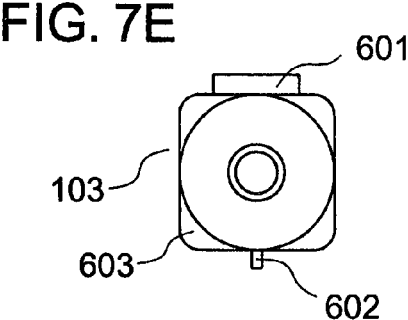
Figure 7F:
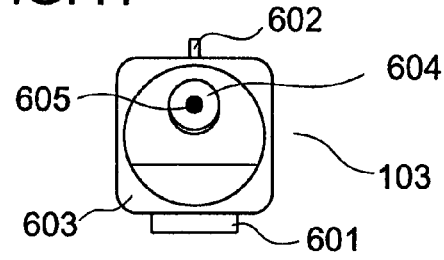

FIG. 12 is a sectional view taken along the line C-C of FIG. 7A, showing the cryostat 103 in this embodiment. The cryostat 103 is filled with liquid helium, and is thermally isolated from the outside via a vacuum layer. A detector coil set 701 is configured in the same way as the detector coil set 12 shown in FIG. 10. In the cryostat 103, each of the detector coils is arranged so as to be parallel with the detection surface 604 of the cryostat 103. Also, on the detection surface 604 of the cryostat 103, the inner layer, the outer layer, and the vacuum layer are fabricated thin as compared with other portions. As the result, the distance between the detector coil surface and the signal source decreases, so that an effect of increased signal intensity is achieved.

Also, the detection surface 604 is provided with a pressure sensor 605 so that a pressure applied to the body surface of examinee by the detection surface 604 can be measured. By this configuration, for example, the contact of the detection surface with the body surface can be detected. Also, by setting a threshold value in advance, an alarm can be sounded or the apparatus can be stopped automatically when a pressure not lower than the threshold value is applied.

Figure 13A:
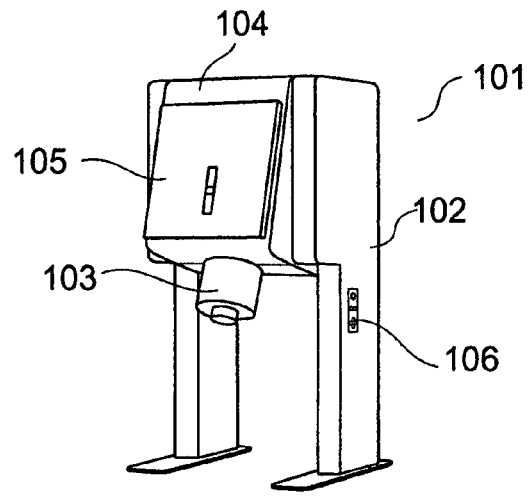
FIGS. 13A to 13C are perspective views of a biomagnetic field measurement apparatus in accordance with an embodiment of the present invention, showing a state in which a gantry and a cryostat oscillate.
Figure 13B:
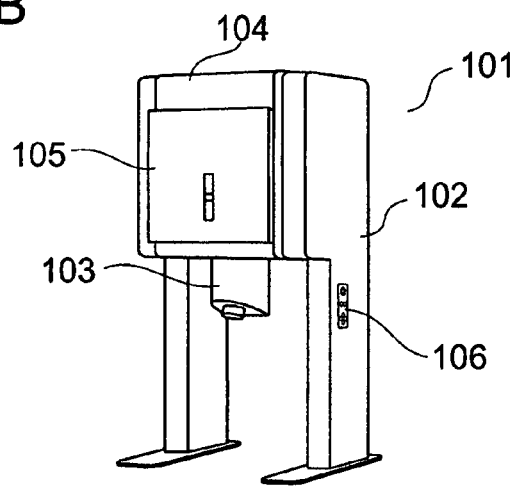
Figure 13C:
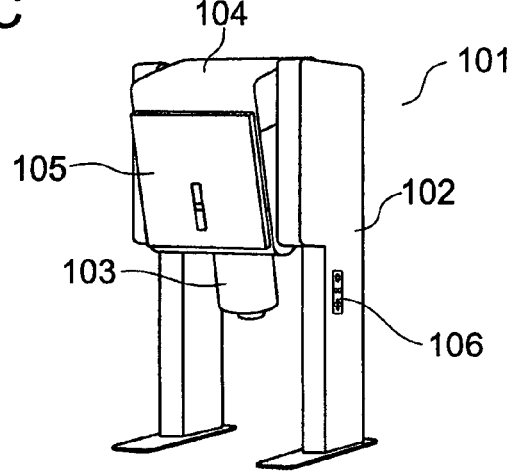

FIGS. 13A to 13C show the state in which the cryostat 103 in this embodiment oscillates. FIG. 13A shows the state in which the cryostat 103 oscillates farthest to the front (oscillation angle: +30 degrees). At this time, the detection surface has an angle of 45 degrees with respect to the horizontal plane. FIG. 13B shows the state in which the second direction is the vertical direction, that is, the cryostat 103 stands upright. FIG. 13C shows the state in which the cryostat 103 oscillates farthest to the rear (oscillation angle: −30 degrees).

The first direction (direction of rotation axis) is substantially perpendicular to the second direction (lengthwise direction) parallel with the axis of the cylindrical cryostat 103, and the detection surface 604 at the tip end of the cryostat 103 oscillates with the first direction being the axis of rotation. The oscillation angle of the axis of the cryostat 103 with respect to the vertical direction is in the range of +30 degrees to −30 degrees.

Figure 14A:
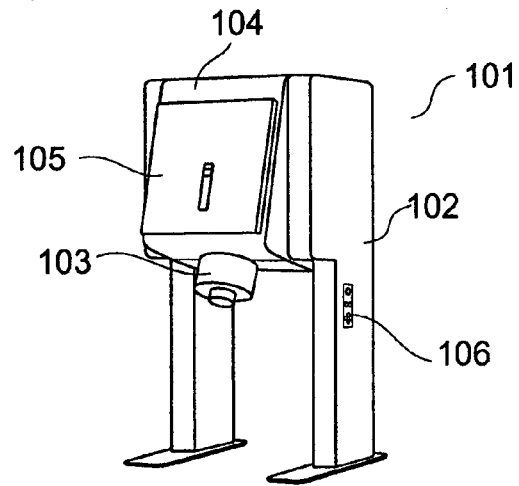
FIGS. 14A to 14C are perspective views of a biomagnetic field measurement apparatus in accordance with an embodiment of the present invention, showing a state in which a cryostat moves in the axial direction of the cryostat.
Figure 14B:
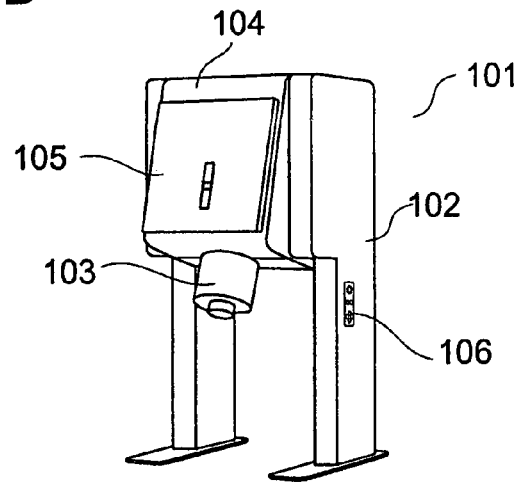
Figure 14C:
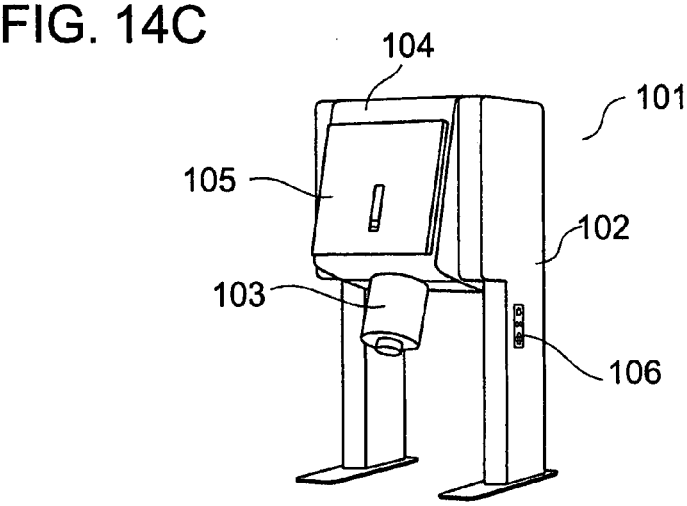

FIGS. 14A and 14C show the state in which the cryostat 103 in this embodiment is expanded and contracted. FIG. 14A shows the state in which the cryostat 103 is contracted most, FIG. 14C shows the state in which the cryostat 103 is expanded most, and FIG. 14B shows an intermediate state. The cryostat 103, which is fixed to the third support 302, is driven in the second direction by the driving means 501 (refer to FIG. 5). In this embodiment, the cryostat 103 can be moved through a distance of 20 cm in the second direction. More specifically, in the state in which the cryostat 103 stands upright (the state shown in FIG. 13B), the detection surface 604 is expanded and contracted in the range of about 70 cm to about 90 cm of the height from the floor surface.

Figure 15A:
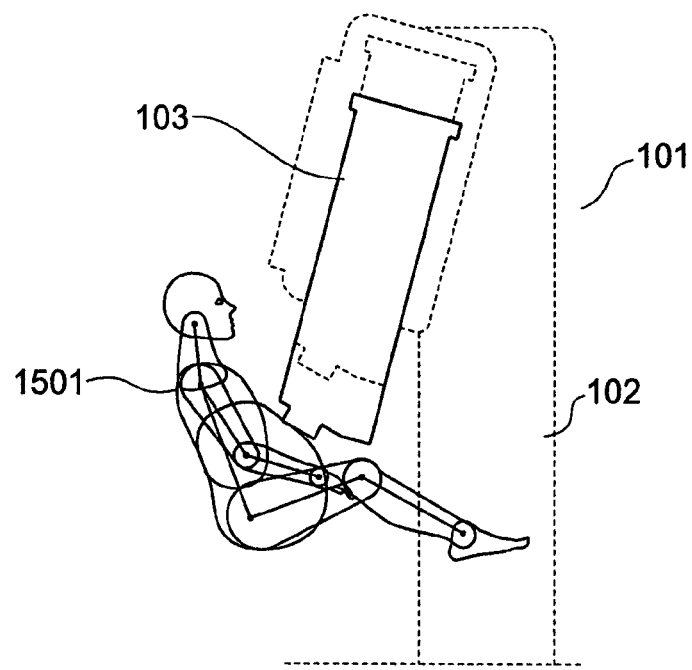
FIGS. 15A and 15B are schematic views showing the positional relationship between a cryostat and a pregnant woman, who is an examinee, at the time when the heart magnetic field of unborn child is measured by using a biomagnetic field measurement apparatus in accordance with an embodiment of the present invention, FIG. 15A showing a state in which the heart magnetic field of unborn child is measured while the pregnant woman adopts a sitting posture, and FIG. 15B showing a state in which the heart magnetic field of unborn child is measured while the pregnant woman adopts a posture of lying on her back.
Figure 15B:
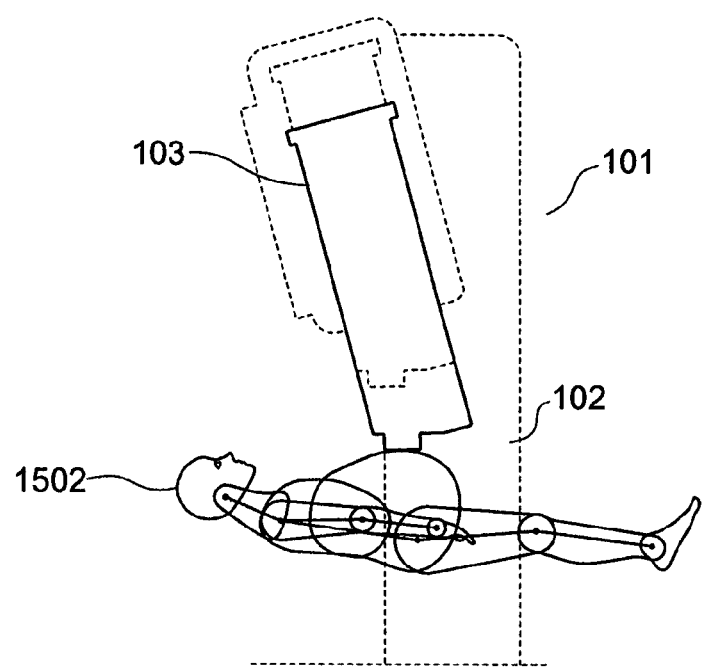

FIGS. 15A and 15B are schematic views showing the positional relationship between the cryostat and a pregnant woman, who is an examinee, at the time when the heart magnetic field of unborn child is measured by using a biomagnetic field measurement apparatus in this embodiment. FIG. 15A shows the state in which the heart magnetic field of unborn child is measured while the pregnant woman adopts a sitting posture. In the state in which an examinee 1501 adopts a sitting posture, the body surface of abdomen has an angle of 30 degrees or larger with respect to the horizontal plane even in the state in which the examinee 1501 leans back in her chair. For the biomagnetic field measurement apparatus 101 of this embodiment, the cryostat 103 can be tilted by an easy operation so that the detection surface 604 has an angle of 45 degrees at a maximum with respect to the horizontal plane. FIG. 15B shows the state in which the heart magnetic field of unborn child is measured while the pregnant woman adopts a posture of lying on her back. In the case where the detection surface 604 is adjusted so as to be substantially parallel with the horizontal plane, the adjustment can be made by tilting the cryostat 103 to the rear through 15 degrees.

Further, the cryostat position indicator 107 provided in the gantry front cover 105 moves in the axial direction of the cryostat 103 in association with the expansion and contraction of the cryostat 103. As the result, the position of the cryostat 103 can be checked easily. Also, by recording the position in the expansion and contraction direction and the tilt angle of the cryostat 103, the position at the measurement time can be reproduced.

To improve the field of vision during operation of an operator (doctor or engineer), each of the two leg parts of the first support 102 of the gantry has a notch part 110 provided on the side on which the examinee is positioned. By this notch part 110, the operator can drive the cryostat 103 by means of the controller 106 while visually checking, from the side, the positional relationship between the detection surface 604 of the cryostat 103 and the body surface of the examinee.

Also, when the detection surface 604 is properly positioned on the body surface of the examinee 1501 or 1502, in this embodiment in which the cryostat 103 expands and contracts in the second direction, the positioning work can be performed easily, and also less sense of oppression and sense of fear are given to the examinee as compared with the method in which the gantry or the bed moves up and down in the vertical direction.

Figure 16A:
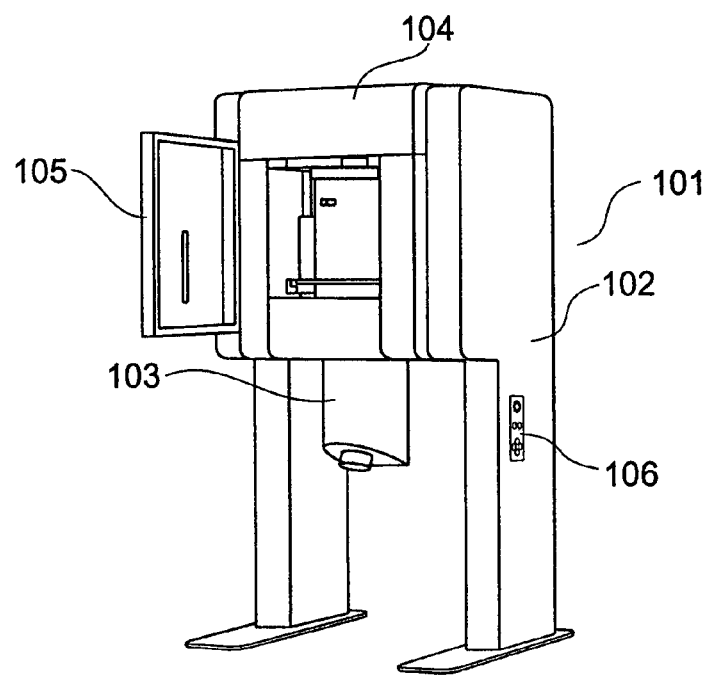
FIGS. 16A and 16B are perspective views showing the state of a gantry at the time when a cryostat in accordance with an embodiment of the present invention is serviced, FIG. 16A showing a state in which a gantry front cover 105 is opened, and FIG. 16B showing a state in which a part of a gantry cover 104 is removed from the state shown in FIG. 16A so that the cryostat can be taken out by being pulled toward a maintenance worker.
Figure 16B:
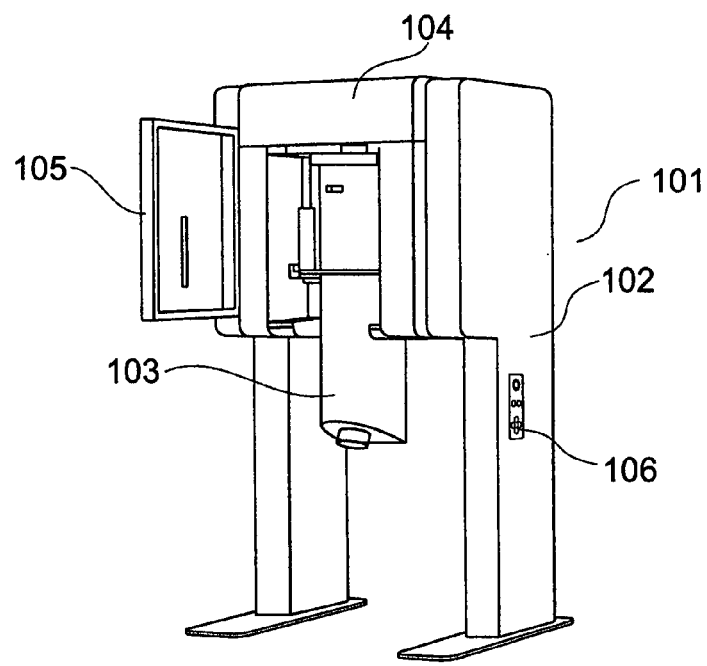

FIGS. 16A and 16B are perspective views showing the state of the gantry at the time when the cryostat 103 in this embodiment is serviced. FIG. 16A shows a state in which the gantry front cover 105 is opened. The main maintenance work for the cryostat 103 is evacuation and filling of liquid helium. In this embodiment, to eliminate the need for removal of the gantry front cover 105, the construction is made so that the gantry front cover 105 is fixed to the first support 102 by using hinges so that the gantry front cover 105 can be opened by using the hinges. This hinge construction can make the maintenance of the cryostat 103 easier. FIG. 16B shows the state in which a part of a gantry cover 104 is removed from the state shown in FIG. 16A. In this state, the cryostat 103 can be removed from the gantry merely by removing screws that fix the intermediate flange 603 to the third support 302 and by pulling the cryostat 103 toward the maintenance worker.

Figure 17:
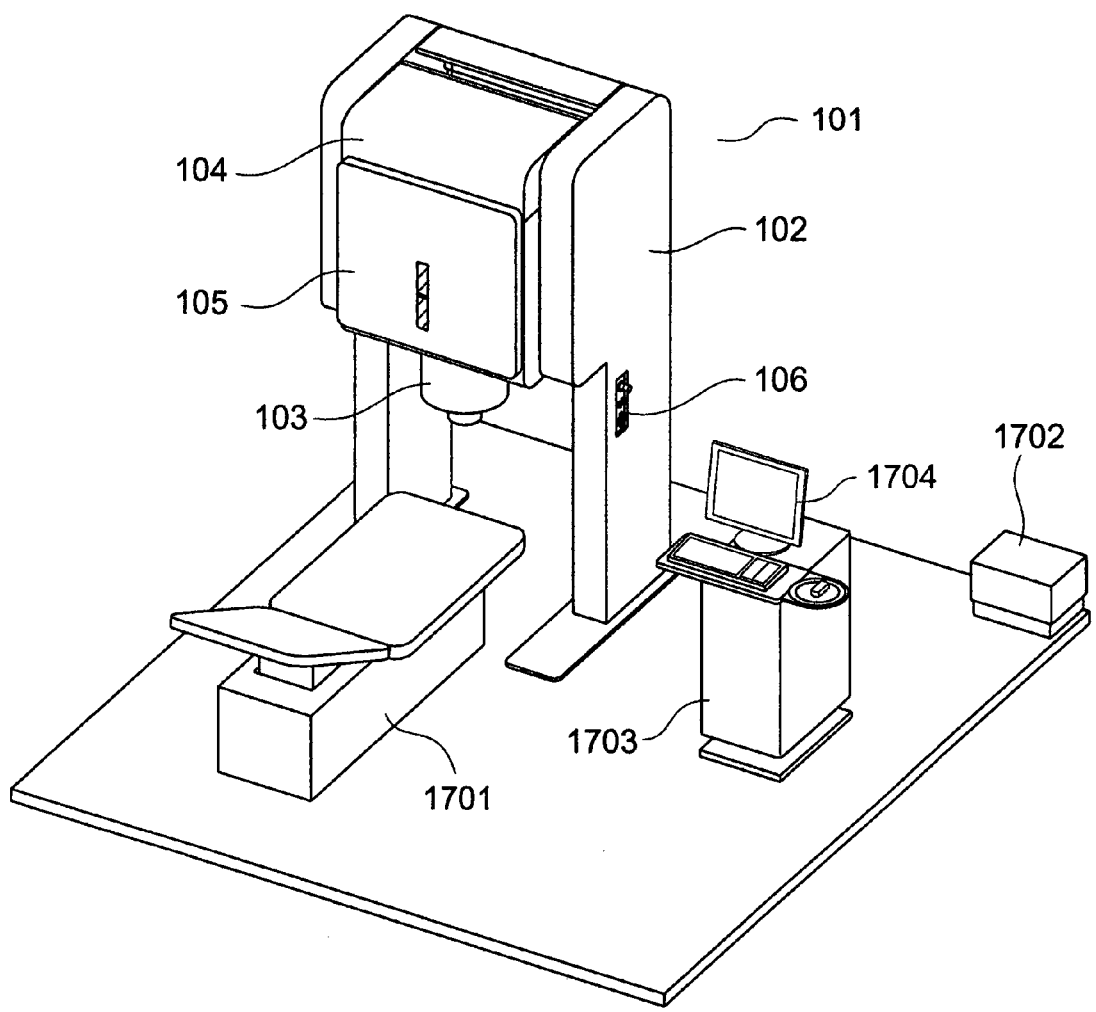
FIG. 17 is a perspective view of a measurement apparatus for measuring the heart magnetic field of unborn child in accordance with an embodiment of the present invention.

FIG. 17 is a perspective view of a measurement apparatus for measuring the heart magnetic field of unborn child in this embodiment.

The detector coil 1 shown in FIG. 8 or the detector coil 2 shown in FIG. 9, and the SQUID are kept at a temperature not higher than the superconductive transition temperature of the superconductive substance that forms the SQUID in the cryostat 103. Specifically, the cryostat 103 is filled with liquid helium, and is thermally isolated from the outside via the vacuum layer. In this embodiment, one set of the two detector coils 2 shown in FIG. 9 is arranged as the detector coil set 12 shown in FIG. 10. Each of the detector coils is arranged so that the detector coil surface is parallel with the detection surface 604 of the cryostat 103.

The cryostat 103 is supported on the gantry. Also, the cryostat 103 is driven so as to oscillate and so as to expand and contract by the gantry. The cryostat 103 is driven by the control of a hydraulic pump. Specifically, a solenoid valve in a hydraulic control unit 1702 is controlled by using the controller 106, by which a pressure is transmitted to the hydraulic cylinders provided in the gantry to drive the driving means 401*a*, 401*b* and 501 of the gantry shown in FIGS. 4 and 5. The oscillating drive is controlled by converting the linear motion of the driving means 401*a*, 401*b* into rotational motion by the crank 402*a*, 402*b*.

To enable the measurement both in the state in which the examinee adopts a posture of lying on his/her back and in the state in which he/she adopts a sitting posture, a bed 1701 has a reclining mechanism so that the angle of a seat back can be changed arbitrarily. By using the controller 106, the detection surface 604 of the cryostat 103 is adjusted so as to be brought close to the abdomen of the examinee.

The SQUID fluxmeter is controlled by the FLL circuit 601 fixed to the cryostat 103, by which the magnetic signals detected by the detector coil are converted into voltage signals, and the converted voltage signals are transmitted to a signal processing device 1703. In the signal processing device 1703, the processing for removing noise signals by using a DSP is performed and biomagnetic signals of the examinee are detected. A heart magnetic field waveform is displayed on a display 1704 in real time. Also, the electrocardiogram waveform of mother's body is measured simultaneously, and is sent to the signal processing device 1703. By performing signal processing, only the heart magnetic field signals of unborn child are extracted from the heart magnetic field signals of both of mother's body and unborn child. Only the heart magnetic field waveform of unborn child is displayed in real time, and also the peaks are detected to display the heart rate of unborn child in real time.

Figure 18:
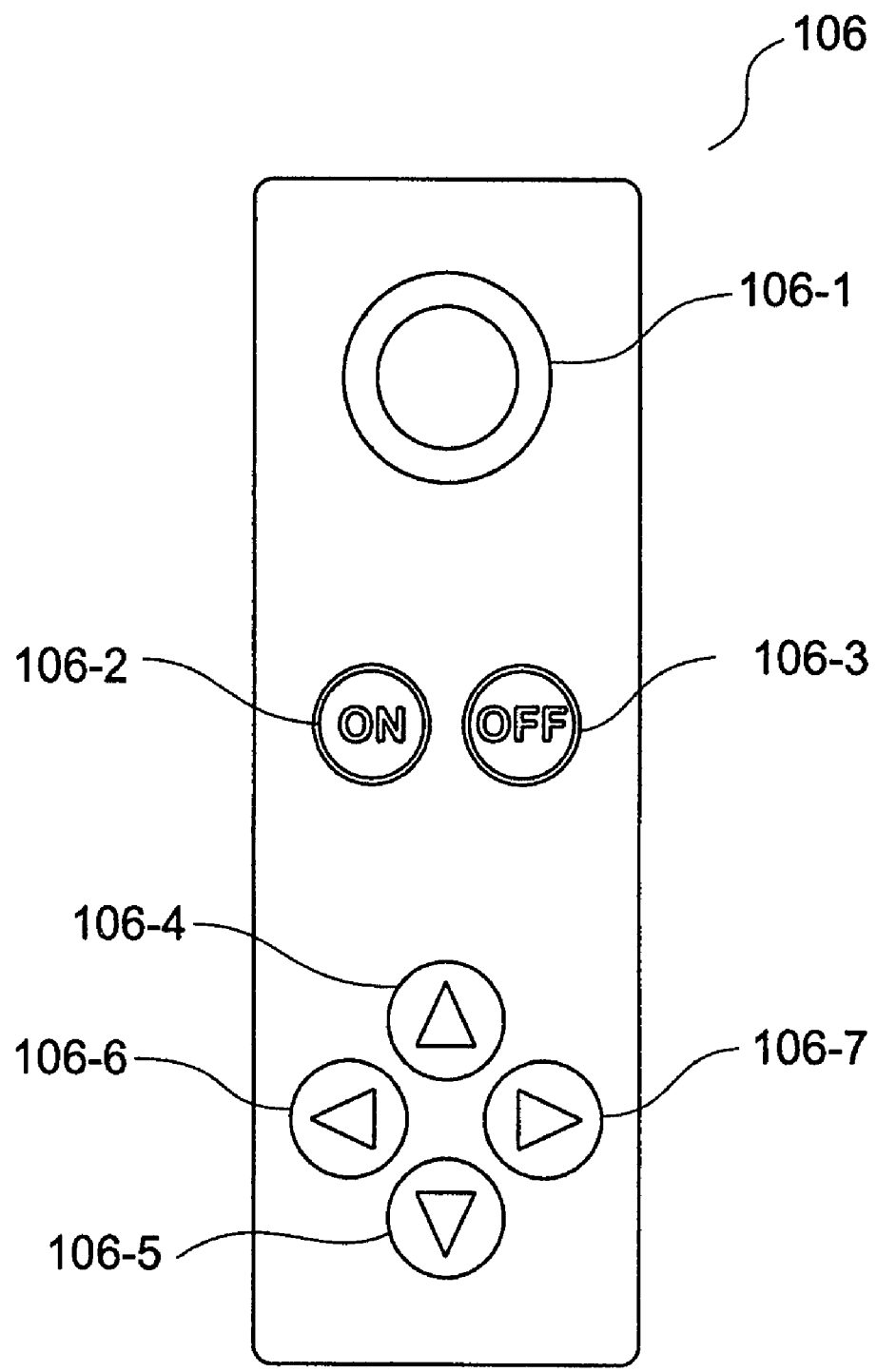
FIG. 18 is a perspective view of a controller for operating a gantry in accordance with an embodiment of the present invention.

FIG. 18 is a perspective view of the controller 106 for operating the gantry in this embodiment. At the measurement time, an ON switch 106-2 is pressed, by which the power source of the hydraulic control unit 1702 is turned ON. The cryostat 103 is driven upward in the second direction (in the direction in which the cryostat 103 exposed from the gantry cover 104 shortens) by pressing an operation button 106-4, and is driven downward in the second direction (in the direction in which the cryostat 103 exposed from the gantry cover 104 lengthens) by pressing an operation button 106-5. Also, the cryostat 103 is oscillatingly driven forward (in the left direction as viewed from the position of the controller 106) by pressing an operation button 106-6, and is oscillatingly driven rearward (in the right direction as viewed from the position of the controller 106) by pressing an operation button 106-7. When the measurement is finished, an OFF switch 106-3 is pressed, by which the power source of the hydraulic control unit 1702 is turned OFF. An emergency stop button 106-1 is used to stop the apparatus in case of emergency.

FIGS. 19 to 24 are views of screens displaying signals obtained in the measurement apparatus for measuring the heart magnetic field of unborn child in this embodiment.

Figure 19:
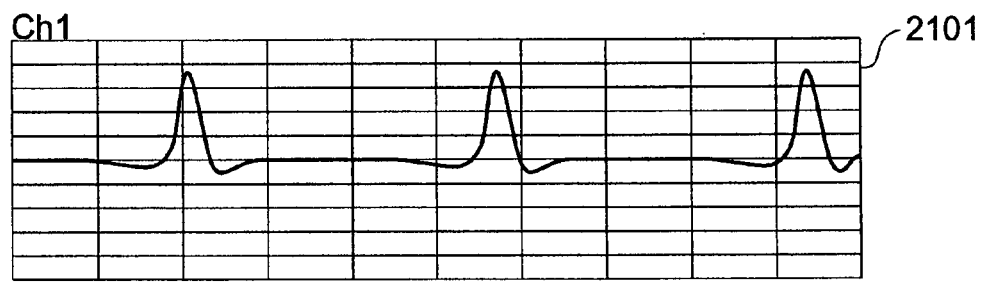
FIG. 19 is graphs showing time-related waveforms obtained from two sensors held in a cryostat.

FIG. 19 is graphs showing time-related waveforms obtained from two sensors. The abscissas of each of the graphs represent time, and the ordinates thereof represent an output signal (magnetic field) of each of the SQUID fluxmeters. The waveforms 2101 and 2102 are an output of a first SQUID fluxmeter held in the cryostat 103 (Ch 1) and an output of a second SQUID fluxmeter held therein (Ch 2), respectively. By this display, a change in magnetic field can be represented most simply.

Figure 20:
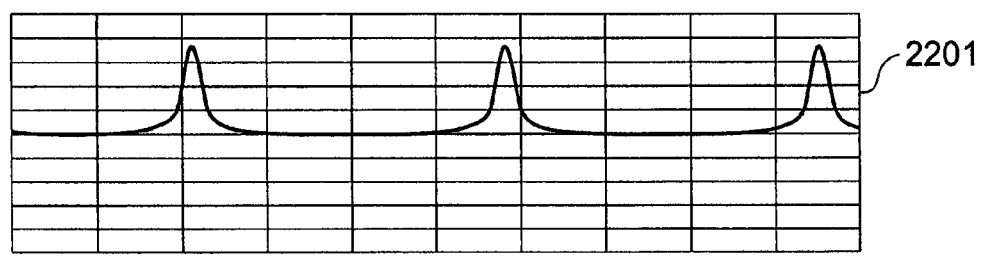
FIG. 20 is a graph showing the magnitude of an electric current vector obtained from the outputs of two sensors held in a cryostat.

FIG. 20 is a graph showing a time-related waveform of signal obtained by adding, in terms of vector, the outputs of two SQUID fluxmeters held in the cryostat. The abscissas of the graph represent time, and the ordinates thereof represent the vector sum of output signals (magnetic fields) of the two SQUID fluxmeters held in the cryostat 103. A waveform 2201 is the vector sum obtained by combining the output of the first SQUID fluxmeter held in the cryostat 103 (Ch 1) with the output of the second SQUID fluxmeter held therein (Ch 2) by using Expression 3. This representing method is suitable for detecting the peaks of waveform. For example, the detection of peak time, the determination of waveform period, or the detection as averaging trigger signal can be carried out easily.

FIG. 21 is graphs showing an electric current vector obtained from the outputs of the two SQUID fluxmeters held in the cryostat 103 and time-related waveforms of the magnitude and phase of an electric current vector. An electric current vector 2303 is a vector representing the direction and magnitude of an electric current calculated by using Expression 5 and the outputs of the two SQUID fluxmeters held in the cryostat 103 (Ch 1 and Ch 2). A waveform 2301 is the same as the waveform 2201 shown in FIG. 20, and corresponds to the magnitude of the electric current vector 2303. Also, a waveform 2302 shows the phase of the electric current vector 2303. The abscissas of both the graphs showing the waveform 2301 and the waveform 2302 represent time. By the display of the electric current vector 2303, the electric current flowing in the living body can be checked intuitively. Also, by the display of the waveform 2301 and the waveform 2302, the electric current flowing in the body can be evaluated more quantitatively.

Figure 22:
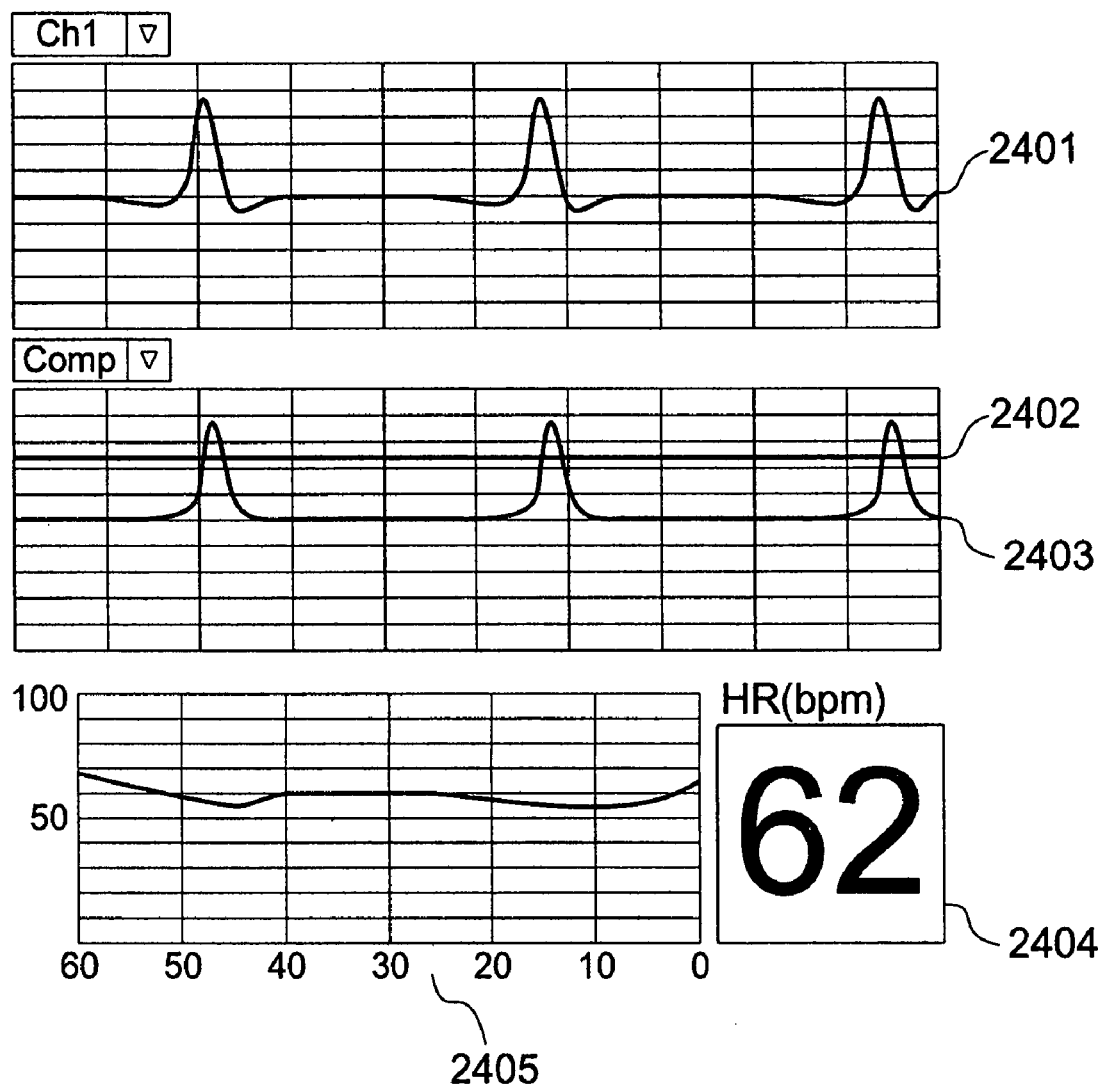
FIG. 22 is a graph showing a waveform selected from the outputs of two sensors held in a cryostat or external input signals (upper diagram), a graph showing a waveform selected from the outputs of two sensors held in the cryostat or external input signals and showing a threshold value for peak detection (middle diagram), a view showing a heart rate that is determined as the number of peaks per one minute by detecting peaks from the waveform in the middle diagram (right-hand side of lower diagram), and a graph showing the history of heart rates displayed on the right-hand side of lower diagram (left-hand side of lower diagram)

In FIG. 22, a waveform 2401 in the upper graph shows the output of the first SQUID fluxmeter held in the cryostat (Ch 1). A waveform 2403 in the middle graph (Comp) is the same as the waveform 2301 shown in FIG. 21, and the peak time is detected automatically by software by taking the maximum value in each time zone that is larger than a threshold value 2402 of peak detection as a peak. At the lower right, a heart rate 2404 that is determined as the number of peaks per one minute by detecting peaks from the waveform 2403 in the middle graph is shown. At the lower left, a history 2405 of the heart rate 2404 shown at the lower right is shown as a graph. The abscissas of the lower left graph represent time (minute) before the present time, and the ordinates represent heart rate. By the history 2405 of the heart rate, a change in heart rate of the examinee (mother's body or unborn child) can be monitored. Also, the upper and middle graphs can be changed over to the display of an external input signal such as other channels or an electrocardiogram.

Figure 23:
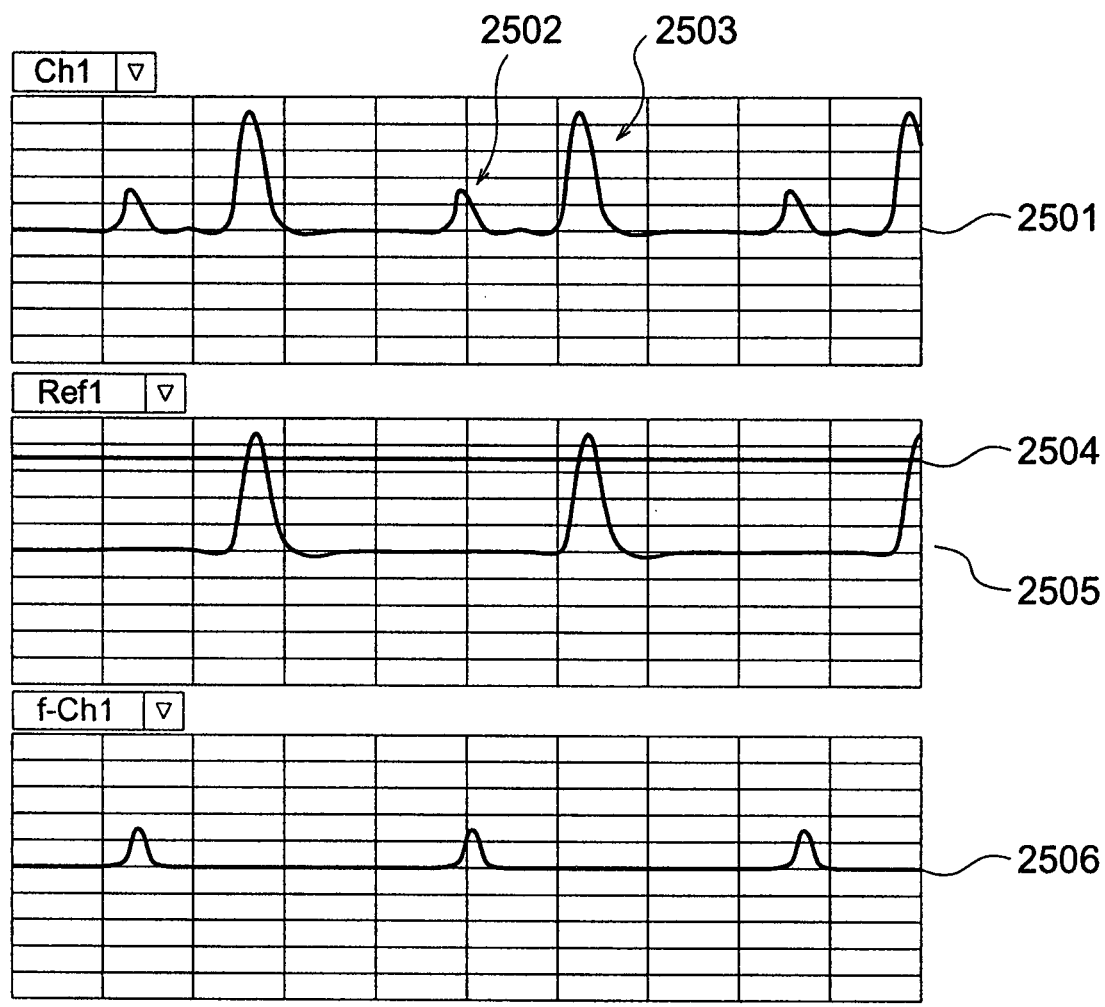
FIG. 23 is a graph showing a signal obtained from the outputs of two sensors held in a cryostat, including heart magnetic field signals of mother's body and unborn child (upper diagram), an electrocardiogram of mother's body (middle diagram), and a graph obtained by removing the heart magnetic field waveform coming from mother's body and extracting the heart magnetic field waveform coming from unborn child (lower diagram)

FIG. 23 shows a screen on which the heart magnetic field waveform of unborn child is extracted and displayed. In FIGS. 20 to 22, the representing methods in the case where the signal coming from either mother's body or unborn child is dominant have been explained. In FIG. 23, the representing method in the case where signals coming from mother's body and unborn child coexist is explained. The upper graph shows an output 2501 of the first SQUID fluxmeter held in the cryostat 103 (Ch 1). The output 2501 of the first SQUID fluxmeter includes a heart magnetic field waveform 2502 coming from mother's body and a heart magnetic field waveform 2503 coming from unborn child. A waveform 2505 in the middle graph shows an external input signal waveform (Ref 1), and the peak time is detected automatically by software by taking the maximum value in each time zone that is larger than a threshold value 2504 of peak detection as a peak. In this case, as the external input signal, the electrocardiogram waveform of mother's body is inputted. In the lower part of FIG. 23, a graph 2506 in which the heart magnetic field waveform coming from mother's body is removed by using the method described below and the heart magnetic field waveform coming from unborn child is extracted (f-Ch 1) is shown.

First, by utilizing non-correlation between the heart magnetic field waveform of mother's body and the heart magnetic field waveform of unborn child, unprocessed waveforms are averaged by using the electrocardiogram waveform of mother's body as a trigger, and further the baseline is corrected so that both ends of the averaged waveform are zero, by which a template heart magnetic field waveform of mother's body is prepared. Since the heart magnetic field waveform of unborn child is removed by the averaging, this template heart magnetic field waveform scarcely includes the signal coming from unborn child. By subtracting the template heart magnetic field waveform of mother's body prepared from the unprocessed waveform by using the electrocardiogram waveform of mother's body as a trigger, the heart magnetic field waveform of unborn child can be extracted.

Figure 24:
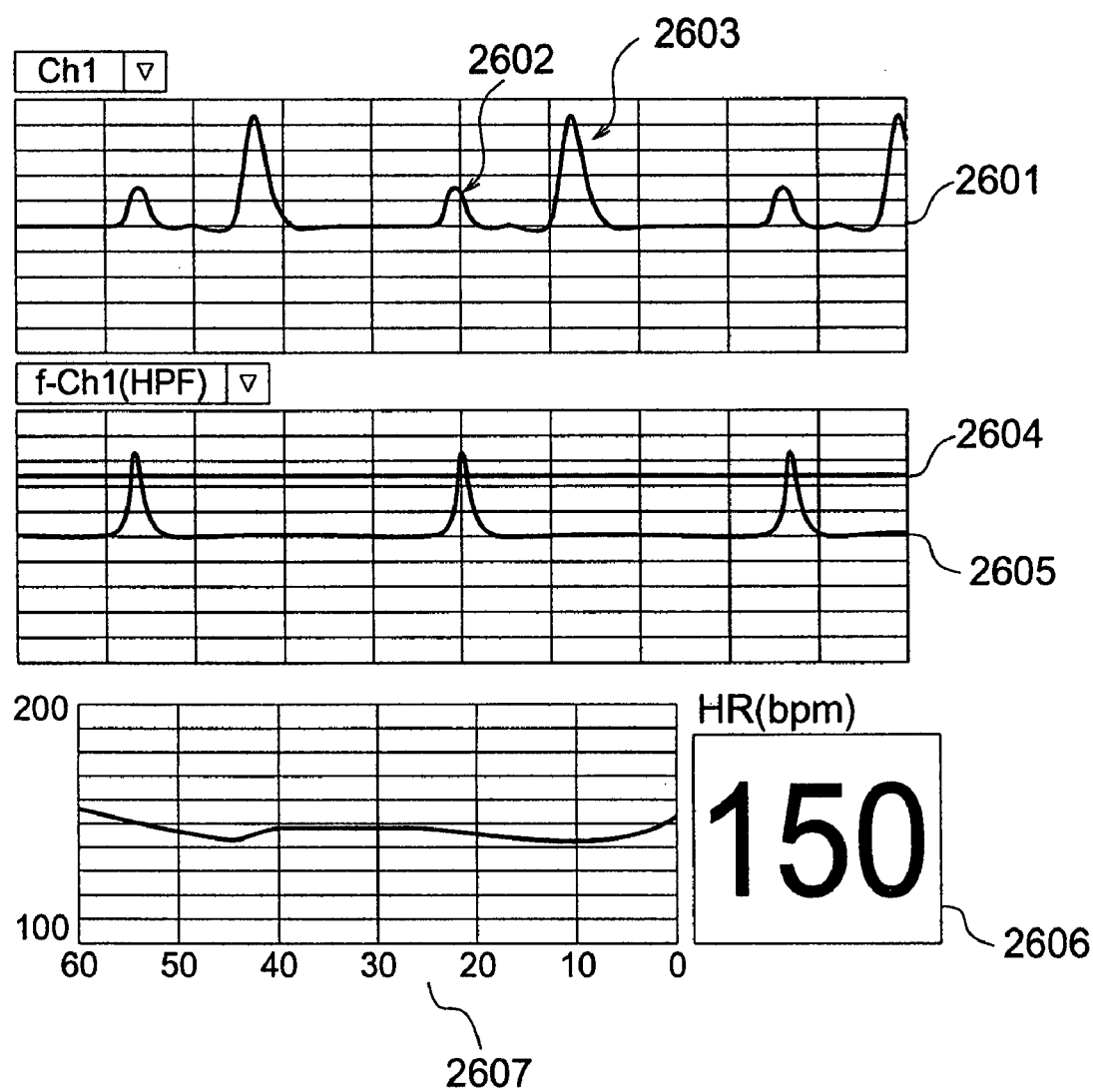
FIG. 24 is a graph showing a signal obtained from the outputs of two sensors held in a cryostat, including heart magnetic field signals of mother's body and unborn child (upper diagram), a graph showing a waveform subjected to high-pass filtering after the heart magnetic field waveform coming from mother's body has been removed and the heart magnetic field waveform coming from unborn child has been extracted (middle diagram), a view showing a heart rate of unborn child that is determined as the number of peaks per one minute by detecting peaks from the waveform in the middle diagram (right-hand side of lower diagram), and a graph showing the history of heart rates of unborn child displayed on the right-hand side of lower diagram (left-hand side of lower diagram).

FIG. 24 shows a screen on which the heart rate of unborn child is displayed. The upper graph shows an output 2601 of the first SQUID fluxmeter held in the cryostat (Ch 1). The output 2601 of the first SQUID fluxmeter includes a heart magnetic field waveform 2602 coming from mother's body and a heart magnetic field waveform 2603 coming from unborn child. The middle graph shows a waveform 2605 obtained by subjecting the heart magnetic field waveform of unborn child obtained in FIG. 23 to high-pass filtering of a cutoff frequency of 3 Hz (f-Ch 1(HPF)). The peak time is detected automatically by software by taking the maximum value in each time zone that is larger than a threshold value 2604 of peak detection as a peak. At the lower right, a heart rate 2606 of unborn child that is determined as the number of peaks per one minute by detecting peaks from the waveform 2605 in the middle graph is shown. At the lower left, a history 2607 of the heart rate 2606 of unborn child shown at the lower right is shown as a graph. The abscissas of the lower left graph represent time (minute) before the present time, and the ordinates represent heart rate. By the history 2607 of the heart rate, a change in heart rate of unborn child can be monitored.

In the embodiment of detector coil of this embodiment explained above, the detector coil subjected to first-order differentiation or second-order differentiation in the vertical direction has been explained as an example. However, the detector coil may be subjected to, for example, third-order or higher-order differentiation in the vertical direction.

Also, in the embodiment explained above, the SQUID fluxmeter is taken as an example as a fluxmeter for converting the magnetic flux detected by the detector coil into a voltage value. However, as the fluxmeter, a magnetoresistive element, giant magnetoresistive element, flux gate fluxmeter, optical pumping fluxmeter, and other types of fluxmeters may be used. Also as the SQUID, an example in which cooling is performed by using liquid helium has been explained. However, if a refrigerator or a SQUID formed by a high-temperature superconductive member is used, liquid nitrogen may be used to perform cooling.

According to this embodiment, in measuring the heart magnetic field of unborn child, the positioning of the sensor surface can be performed safely and exactly. Specifically, by driving the cryostat so as to oscillate and expand and contract, a biomagnetic field measurement apparatus can be realized which is capable of monitoring the heart rate of unborn child easily in the state in which the abdomen of mother's body adopts a sitting posture or a posture of lying on her back at an arbitrary position.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A biomagnetic field measurement apparatus, comprising:
    a portal first support having two leg parts and a connecting part that connects upper parts of the two leg parts to each other;
    a cylindrical cryostat provided between the two leg parts under the connecting part;
    a detection sensor for detecting a biomagnetic field, which is placed medially in the cryostat and comprising a detector coil set positioned close to a tip end of the cryostat;
    a second support which is rotatably supported on the first support along an axis in a direction connecting the two leg parts of the portal first support and configured to control the tilt of the cryostat;
    a third support holding the cylindrical cryostat and being supported on rails formed on the second support and configured to control axial movement of the cryostat;
    driving units for driving the second and third supports respectively; and
    a control unit for controlling the driving units,
    wherein the first support forms a portal construction having an open space, which accommodates an examinee, between the two leg parts and under where the cryostat is provided.

2. The biomagnetic field measurement apparatus according to claim 1, wherein each of the two leg parts is posteriorly located in comparison with the cylindrical cryostat.

3. The biomagnetic field measurement apparatus according to claim 1, wherein the first support has a gantry front cover provided on the second support.

4. The biomagnetic field measurement apparatus according to claim 1, wherein at least one of the driving units is a cylinder.

5. The biomagnetic field measurement apparatus according to claim 1, wherein at least a part of the detector coil set is placed in a projection portion of the cryostat which is projecting from a cylinder tip plane of the cryostat.

6. The biomagnetic field measurement apparatus according to claim 1, wherein the detection sensor transmits a magnetic signal detected by a magnetism detector coil comprising a superconductor or a metallic member to a superconducting quantum interference device.

7. The biomagnetic field measurement apparatus according to claim 6, wherein the magnetism detector coil is comprising a superconductor or a metallic member, and is configured so that a plurality of differential coils having a different loop direction are arranged in parallel at predetermined intervals and are connected to each other.

8. The biomagnetic field measurement apparatus according to claim 7, wherein the plurality of differential coils are two differential coils.

9. The biomagnetic field measurement apparatus according to claim 7, wherein at least one of the differential coils is a second-order differential coil.

10. The biomagnetic field measurement apparatus according to claim 7, wherein at least one of the differential coils is a first-order differential coil.

11. The biomagnetic field measurement apparatus according to claim 6, wherein the superconductor or metallic member is a wire.

12. The biomagnetic field measurement apparatus according to claim 6, further comprising a second magnetism detector coil which intersects with the magnetism detector coil to consist a set of two of the magnetism detector coils.

13. The biomagnetic field measurement apparatus according to claim 12, wherein the two magnetism detector coils intersect with each other at a right angle.

14. The biomagnetic field measurement apparatus according to claim 1, wherein a sensor for measuring a pressure is provided on a surface of a projecting part of the cryostat.

15. The biomagnetic field measurement apparatus according to claim 1, wherein a tip end part of the cryostat has a first surface and a second surface, the second surface tilting with respect to the first surface to an examinee side, and the detection sensor being provided on the second surface.

* * * * *